US008642039B2

(12) United States Patent
Yarranton

(10) Patent No.: US 8,642,039 B2
(45) Date of Patent: Feb. 4, 2014

(54) **METHOD OF TREATING A STAPHYLOCOCCUS INFECTION IN A PATIENT HAVING A LOW-LEVEL PATHOGENIC *PSEUDOMONAS AERUGINOSA* INFECTION**

(75) Inventor: Geoffrey T. Yarranton, South San Francisco, CA (US)

(73) Assignee: KaloBios Pharmaceuticals, INc., South San Francisco, CA (US)

( * ) Notice: Subject to any disclaimer, the term of this patent is extended or adjusted under 35 U.S.C. 154(b) by 0 days.

(21) Appl. No.: 12/975,214

(22) Filed: Dec. 21, 2010

(65) Prior Publication Data

US 2011/0165172 A1 Jul. 7, 2011

Related U.S. Application Data

(60) Provisional application No. 61/288,977, filed on Dec. 22, 2009.

(51) Int. Cl.
*A61K 39/395* (2006.01)
*A61K 39/40* (2006.01)
*C07K 16/00* (2006.01)
*C12P 21/08* (2006.01)

(52) U.S. Cl.
USPC ............... 424/170.1; 424/130.1; 424/131.1; 424/150.1; 424/164.1; 530/387.1; 530/387.3; 530/391.1

(58) Field of Classification Search
None
See application file for complete search history.

(56) References Cited

U.S. PATENT DOCUMENTS

| 6,827,935 B2 | 12/2004 | Frank et al. |
| 2006/0228384 A1 | 10/2006 | Eldridge |
| 2009/0191186 A1 | 7/2009 | Bebbington et al. |

FOREIGN PATENT DOCUMENTS

| WO | WO 2009/073631 A2 | 6/2009 |
| WO | WO 2010/091189 A2 | 8/2010 |

OTHER PUBLICATIONS

Bendig et al (Methods: A Companion to Methods in Enzymology 1995; 8: 83-93.*
Abbas et al. Cellular and Molecular Immunology 4th edition, 2000 Chapter 48 p. 42-43 and p. 48.*
Brown et al. J immunol. May 1996; 156(9):3285-91.*
Paul, Fundamental Immunology, 3rd Edition, 1993, pp. 292-295.*
Baer, M., et al, "An Engineered Human Antibody Fab Fragment Specific for *Pseudomonas aeruginosa* PcrV Antigen Has Potent Antibacterial Activity," *Infection and Immunity*, vol. 77(3), pp. 1083-1090 (Mar. 2009).
Govan, J., "Infection control in cystic fibrosis: methicillin-resistant *Staphylococcus aureus, Pseudomonas aeruginosa* and the *Burkholderia cepacia* complex," *Journal of the Royal Society of Medicine*, vol. 93(38), pp. 40-45 (2000).
Hendricks, K., et al., "Synergy Between *Staphylococcus aureus* and *Pseudomonas aeruginosa* in a Rat Model of Complex Orthopaedic Wounds," *The Journal of Bone and Joint Surgery*, vol. 83-A(6), pp. 855-861 (2001).
Hoffman, L., et al., "Selection for *Staphylococcus aureus* small-colony variants due to growth in the growth in the presence of *Pseudomonas aeruginosa*," *PNAS*, vol. 103(52), pp. 19890-19895 (Dec. 26, 2006).
Lambert, P.., "Mechanisms of antibiotic resistance in *Pseudomonas aeruginosa*," *Journal of the Royal Society of Medicine*, vol. 95(41), pp. 22-26 (2002).
Magnotti, L., et al., "Efficacy of Monotherapy in the Treatment of Pseudomonas Ventilator—Associated Pneumonia in Patients With Trauma," *Journal of Trauma-Injury Infection & Critical Care*, vol. 66(4), pp. 1052-1059 (Apr. 2009).
Moise, P., et al., "Susceptibility relationship between vancomycin and daptomycin in *Staphylococcus aureus*: facts and assumptions," *Lancet Infect. Dis.*, vol. 9, pp. 617-624 (Oct. 2009).
O'Connell, D., "Bacterial Pathogenesis: Axis of evil," *Nature Reviews: Microbiology*, vol. 5(2), p. 85 (Feb. 1, 2007).
Solh, A., et al., "Diagnostic yield of quantitative endotracheal aspirates in patients with sever nursing home-acquired pneumonia," *Critical Care*, vol. 11(3):R57, pp. 1-6 (2007).
Zapantis, A., et al., "Nationwide Antibiogram Analysis Using NCCLS M39-A Guidelines," *Journal of Clinical Microbiology*, vol. 43(6), pp. 2629-2634 (Jun. 2005).

* cited by examiner

*Primary Examiner* — Oluwatosin Ogunbiyi
(74) *Attorney, Agent, or Firm* — Kilpatrick Townsend & Stockton LLP

(57) ABSTRACT

This invention provides methods of treating patients having a *Staphylococcus* infection where the patient also has a low level of *Pseudomonas aeruginosa*. The methods comprise administering an antagonist of the *Pseudomonas* Type III Secretion System, e.g., an anti-PcrV antibody antagonist.

26 Claims, 5 Drawing Sheets

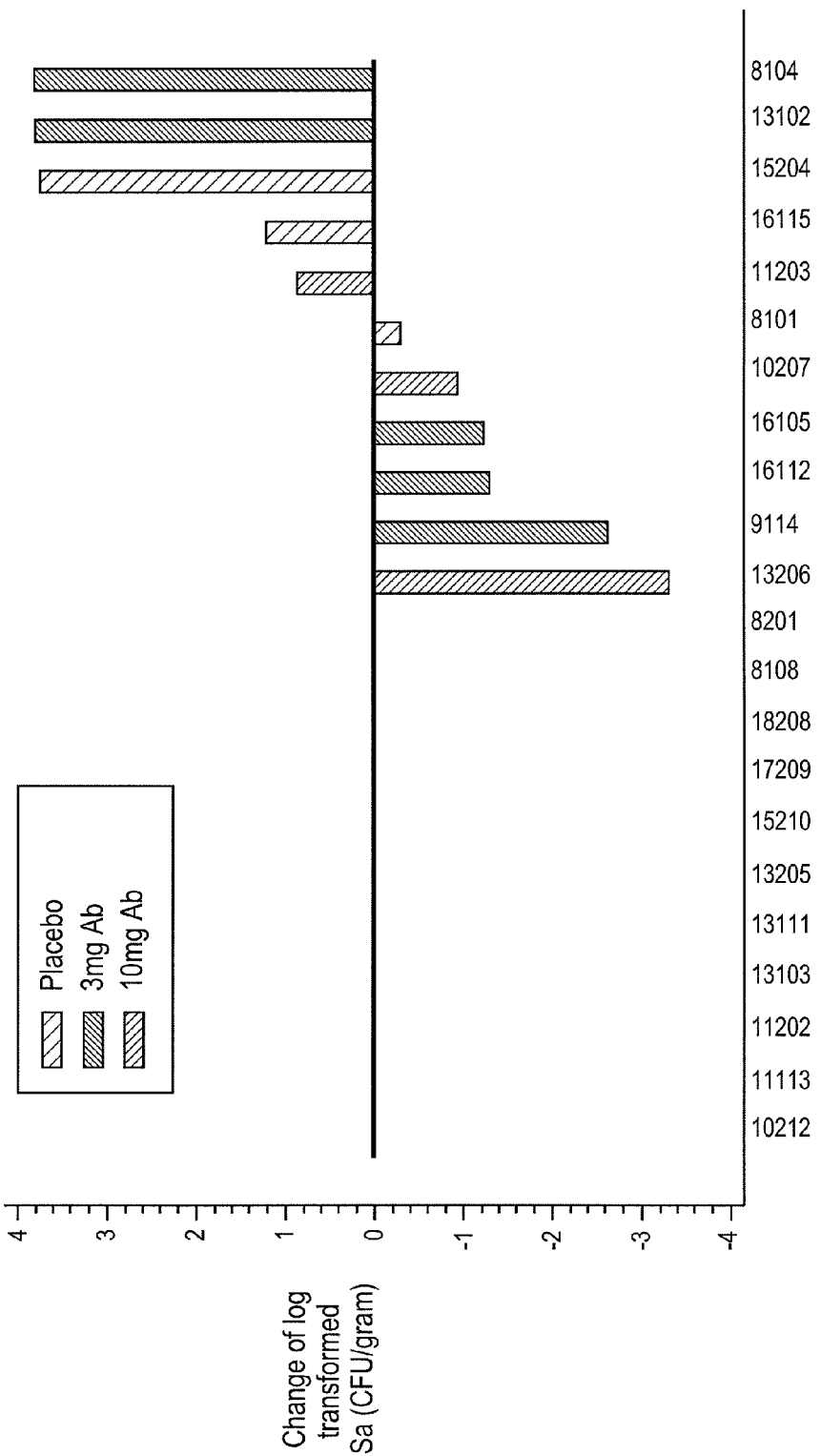

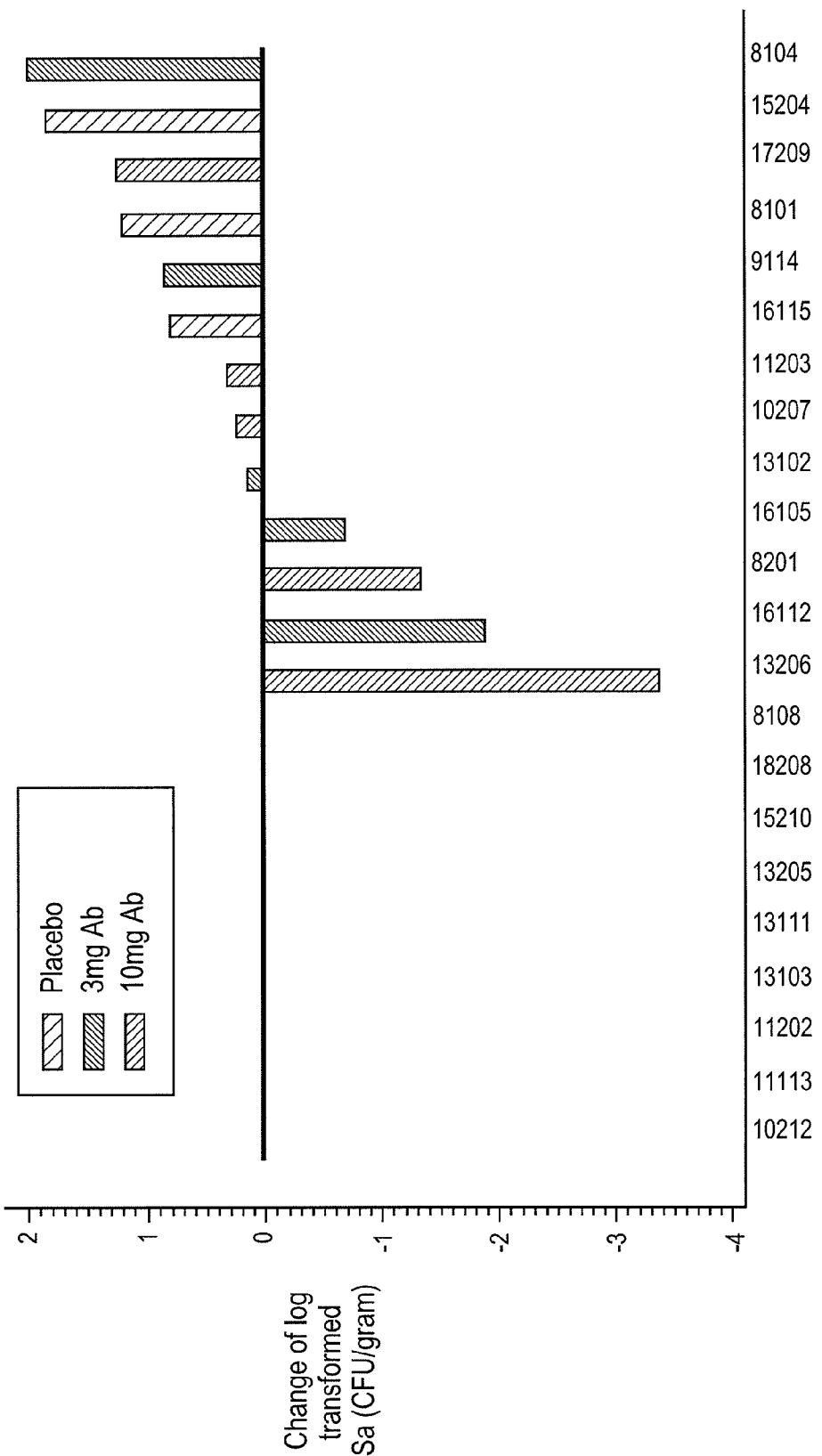

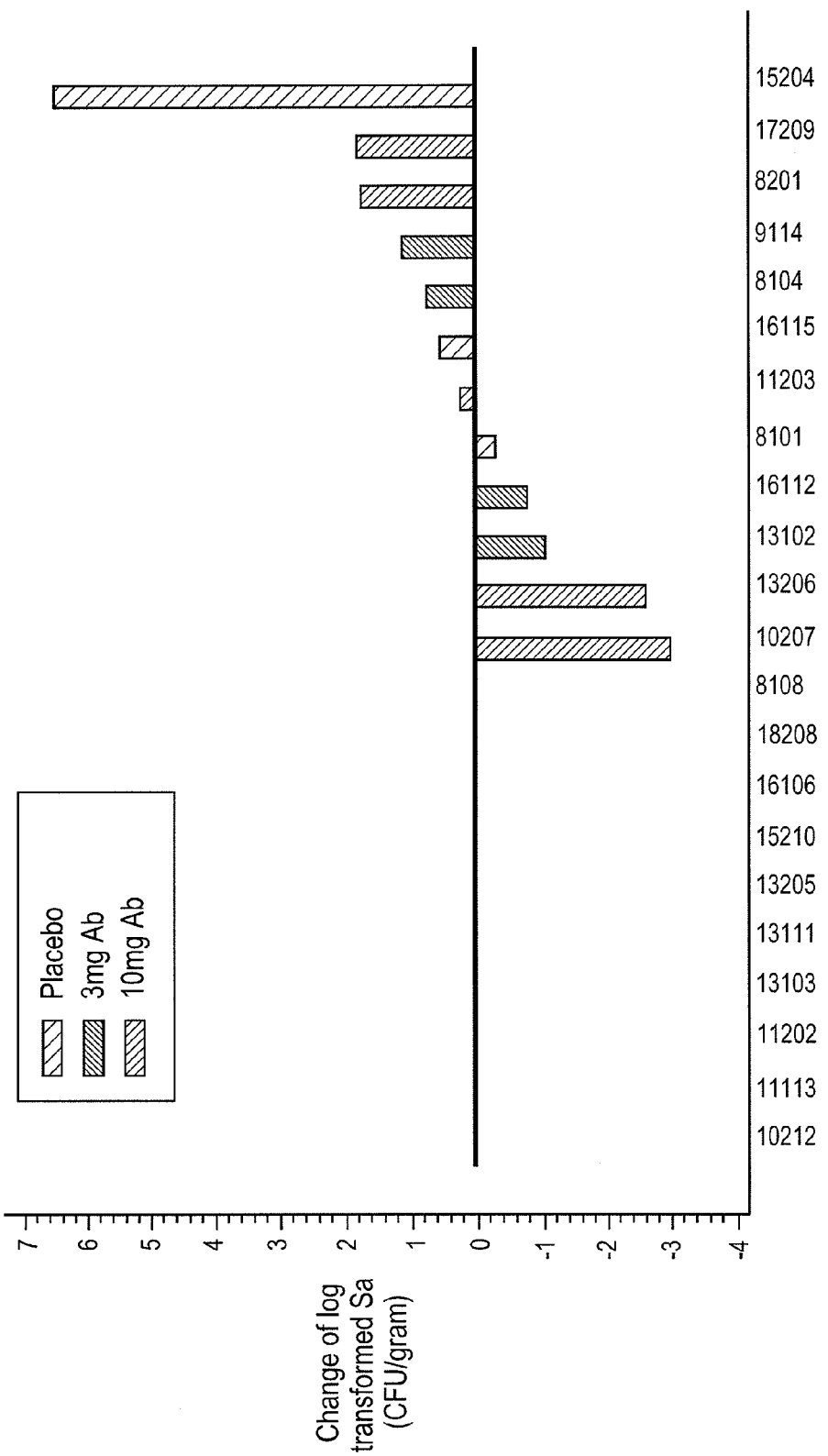

FIG. 4

```
VH1-18   QVQLVQSGAEVKKPGASVKVSCKASGYTFTSYGISWVRQAPGQGLEWMGWISAYNGNTNYAQKLQGRVTMTTDTSTSTAYMELRSLRSDDTAVYYCAR------AFDIWGQGTMVTVSS  JH3
         EI.........................DHA..................P.S.P...S.....SL...R..R.......K.......NRGDIYDFTY.....

VH3 30.3 QVQLVESGGGVVQPGRSLRLSCAASGFTFSSYAMHWVRQAPGKGLEWVAVISYDGSNKYYADSVKGRFTISRDNSKNTLYLQMNSLRAEDTAVYYCAR------AFDIWGQGTMVTVSS  JH3
         .............VG.........GI........W.N.KEIS......V....L......S...T.......NRGDIYDFTY.M.....
         .............VG.........GI........W.N.KEIS......V....P......S...T.......NRGDIYDFTY.M.....
         ..........T..S..........G.........W.N.KEIS......V....P......S...T.......NRGDIYDFTY.M.....
         .E...........G..........TAG.......W.N.KEIS......VF...P......S...T.......NRGDIYDFTY.M.....
         .............G..........TAG.......W.N.KEIS......V....P......S...T.......NRGDIYDFTY.M.....
         .E......................PL........SF.........E....S.........E...P.......NRGDIYDFTY.M.....
         .E......................PL........SF.........E....S.........E...P.......NRGDIYDFTY.M.....
         .E......................PL........SF.........E....S.........E...P.......NRGDIYDFTY.M.....
         .E......................PL........SF.........E....S.........E...P.......NRGDIYDFTY.M.....
         .E......................G.........W...R..........................I.......NRGDIYDFTY.M.....
         .E......................G.........W...Y..D....................P.......NRGDIYDFTY.M.....
         .E.......T...S..........G................................................NRGDIYDFTY.M.....
         .E...........VG.........GI........N.W....SES.I..........V..D.R.V.........NRGDIYDFTY.M.....

.E......................N.P......................................E....P.......------GMDVWGQGTVTVSS  JH6
         .E......................N.P......................................E....P.......NRGDIYDFTY.A..Q.....
         .E......................N.P......................................E....P.......NRGDIYDFTY.A..S.....
         .E......................N.P......................................E....P.......NRGDIYDFTY.A..I.....
         .E......................N.P......................................E....P.......NRGDIYDFTY.A..Y.....
```

FIG. 5

```
VkI L12   DIQMTQSPSTLSASVGDRVTITCRASQSI-SSWLAWYQQKPGKAPKLLIYDASSLESGVPSRFSGSGSGTEFTLTISSLQPDDFATYYCQQYNSYSYTFGQGTKLEIK Jk2
          ...L........S.........EGV-DR......R........T.Q................S............V......HFWGTP.............
          ...SV...................G.-.......R....A......Q.........G.............................E.V....FW.TP.............
          ......F.................G.-.TY....R........SA...Q.......V.D...........SE..V..........E.V....FW.TP.............
          ...L..F.................G.-.TY.................A.Q....................................E.V....FW.TP.............
          ...L..F.................G.-.TY.................A.Q....................................E.V....FW.TP.............
          A..L..F.................G.-.TY.................A..Q...................D...............E.V....FW.TP.............
          ......S.................-.R.V....R...N.........................................................E.I....FW.TP.............
          ......S.................-.R.V....R...N.........................................................E.I....FW.TP.............
          ......S.................-.R.V....R...N.........................................................E.I....FW.TP.............
          ......S.................-.R.V....R............................................................E.I....FWGTP.............
          ...L..........S.........EGV-DR......R....................S.............................V......HFW.TP.............

VkIII L2  EIVMTQSPATLSVSPGERATLSCRASQSV-SSNLAWYQQKPGQAPRLLIYGASTRATGIPARFSGSGSGTEFTLTISSLQSEDFAVYYCQQYNNWPYTFGQGTKLEIK Jk2
          ...L..F.G...L.........N..GAY..................R.P...D.......NR.EP.................FWST.............
          ..........................-......................................................F.A..............................FWST.............
          ..........................-......................................................F.A..............................FWST.............
          ..........................................................................................................FWST.............

VL3 31    SSELTQDPAVSVALGQTVRITCQGDSLRSYYASWYQQKPGQAPVLVIYGKNNRPSGIPDRFSGSSSSGNTASLTITGAQAEDEADYYCNSRDSSGNHVVFGGGTKLTVL J12
          .............T...............L.......................................L.S..S.................R..........QHFW.TP--YT.............
          .............T...........................................................................R..........QHFW.TP--YT.............

VL2 2c    QSALTQPPSASGSPQGSVTISCTGTSSDVGGYNYVSWYQQHPGKAPKLMIYEVSKRPSGVPDRFSGSKSGNTASLTVSGLQAEDEADYCCSSYAGSNNFVFGGGTKLTVL............
          ..V.......................A..............Y..V..I...T.............................................R..........QHFWSTP--YT............
          ..A.V........I...........................-----...........................I.D.TN................................QHFWSTP--YT............
```

METHOD OF TREATING A STAPHYLOCOCCUS INFECTION IN A PATIENT HAVING A LOW-LEVEL PATHOGENIC *PSEUDOMONAS AERUGINOSA* INFECTION

CROSS-REFERENCE TO RELATED APPLICATIONS

This application claims benefit of U.S. provisional application No. 61/288,977, filed Dec. 22, 2009, which application is herein incorporated by reference.

REFERENCE TO A "SEQUENCE LISTING," A TABLE, OR A COMPUTER PROGRAM LISTING APPENDIX SUBMITTED AS AN ASCII TEXT FILE

The Sequence Listing written in file -37-1.TXT, created on Jun. 14, 2013, 57,344 bytes, machine format IBM-PC, MS-Windows operating system, is hereby incorporated by reference in its entirety for all purposes.

BACKGROUND OF THE INVENTION

*Pseudomonas aeruginosa* (*P. aeruginosa*) is an opportunistic pathogen that rarely causes disease in healthy people, but is a significant problem for critically ill immunocompromised individuals or individuals with defective lung epithelial cell clearance of pathogens, e.g. cystic fibrosis (CF) patients. Infection is a major problem in individuals who have CF, where chronic infection of the lung with *P. aeruginosa* causes progressive loss of lung function. In CF patients, it is known that the number of *P. aeruginosa* cells that express the Type III secretion system (TTSS) is a small proportion of the total *P. aeruginosa* burden in the lungs. This may explain why CF patients can tolerate a high bacterial burden in their lungs for many years. However, the TTSS-expressing cells may play an important role in the slow, progressive loss of lung function that leads to early death due to lung failure. Others at risk from *P. aeruginosa* infection include patients on mechanical ventilators, neutropenic cancer patients, and burn patients, where infections are acute and most of the *P. aeruginosa* cells express the TTSS.

Patients at risk for *P. aeruginosa* infection may also have other bacterial infections, e.g., *Staphylococcus aureus* (*S. aureus*) infections. The levels of *P. aeruginosa* and *S. aureus* infection within a patient are commonly perceived as being inversely proportional, i.e., when *P. aeruginosa* levels are high, *S. aureus* levels are low. In particular, it has been observed that as CF patients acquire *P. aeruginosa* chronic infection, *S. aureus* is cultured less frequently from the sputum. Studies have further shown that *P. aeruginosa* simultaneously suppresses the growth and enhances the amino glycoside resistance of *S. aureus* by the production of a compound HQNQ (O'Connell, Nature Reviews Microbiology, Vol. 5, February 2007, Hoffman et al., Proc. Natl. Acad. Sci. USA 103:19890-19895, 2006). It is thus commonly believed that treatment regimens that reduce the level of *P. aeruginosa* provide an opportunity for the *S. aureus* to grow. It may therefore be detrimental to reduce the level of *P. aeruginosa* in patients co-infected with *S. aureus* and *P. aeruginosa* because it creates an environment in which pathogenic *S. aureus* strains can increase, causing patient morbidity and mortality.

One of the virulence mechanisms of *P. aeruginosa* through which cytotoxins are injected into host cells is the type III secretion system (TTSS). The type III secretion system is an important virulence factor in that it inhibits host defense systems and damages epithelial barriers. Upon activation, the type III secretion apparatus translocates toxins into the cytoplasm of the host cell, resulting in cell rounding, lifting, and cell death by necrosis. One method of treating *P. aeruginosa* infection targets the TTSS, e.g., the V antigen of the *P. aeruginosa* TTSS, which is referred to as "PcrV".

Antibodies that target the TTSS have been suggested as therapeutic agents for the treatment of patients with a *P. aeruginosa* infection. The current invention is based, in part, on the surprising discovery that patients that have a *S. aureus* infection and are co-infected with *P. aeruginosa* have reductions in the level of *S. aureus* when treated with an agent that selectively targets the TTSS of *P. aeruginosa*. This is counter to the expectation that *S. aureus* levels would increase if *P. aeruginosa* levels were reduced.

BRIEF SUMMARY OF THE INVENTION

The inventors have discovered that patients that have an *S. aureus* infection in need of treatment for the *S. aureus* infection and that also have a low level of *P. aeruginosa* infection can be treated with a selective antagonist of the *Pseudomonas* TTSS, resulting in a decrease in the level of *S. aureus* in the patient. Thus, in one aspect, the invention provides a method of treating a *S. aureus* infection in a patient that has a low level *P. aeruginosa* infection, the method comprising administering a PcrV antagonist, preferably an anti-PcrV antibody antagonist, of the *P. aeruginosa* TTSS in an amount to effectively reduce the *S. aureus* load in the patient. The patient may have cystic fibrosis or be on a mechanical ventilator. In some embodiments the patient is a neutropenic cancer patient. In some embodiments, the patient is a burn patient. The method of treating the patient can further comprise administering a therapy that targets the *S. aureus* infection. In some embodiments, the method comprises administering an antibiotic, e.g., a penicillinase-resistant penicillin such as oxacillin, nafcillin, cloxacillin, dicloxacillin, or flucoxacillin. In some embodiments, the treatment method further comprises administering vancomycin or daptomycin. In some embodiments the patient has an antibiotic-resistant *S. aureus* infection. In some embodiments the patient has an antibiotic-resistant *P. aeruginosa* infection. In some embodiments both the *S. aureus* and the *P. aeruginosa* infections are antibiotic-resistant. In some embodiments, the patient has cystic fibrosis and a methicillin-resistant *S. aureus* infection. In some embodiments, the patient has cystic fibrosis and a methicillin-sensitive *S. aureus* infection.

In an additional aspect, the invention provides a method of treating a mechanically ventilated patient infected with *Staphylococcus aureus* and *Pseudomonas aeruginosa*, where the levels of *Staphylococcus aureus* and *Pseudomonas aeruginosa* are each about $10^3$ cfu/ml, or less, in an endotrachanel aspirate; or about $10^2$ cfu/ml, or less, in a bronchoalveolar lavage, the method comprising administering an anti-PcrV antibody antagonist of the Type III secretion system.

In a further aspect, the invention provides a method of treating a patient with a wound infected with *Staphylococcus aureus* and *Pseudomonas aeruginosa*, where the levels of *Staphylococcus aureus* and *Pseudomonas aeruginosa* are each less than about $10^3$ cfu/g of tissue or less than about $10^3$ cfu/ml of exudate, the method comprising administering an anti-PcrV antibody antagonist of the Type III secretion system.

In some embodiments, the treatment methods of the invention comprise administering an anti-PcrV antibody that competes with Mab 166 for binding to PcrV.

In some embodiments, the treatment methods of the invention comprise administering an anti-PcrV antibody that has a $V_H$ CDR3 that comprises NRGDIYYDFTYAMDX (SEQ ID NO:45), wherein X is I, Q, Y, or S; and a $V_L$ CDR3 that comprises FW(S/G)TP (SEQ ID NO:46), e.g., QQFWSTPYT (SEQ ID NO:47), QHFWGTPYT (SEQ ID NO:48), or QHFWSTPYT (SEQ ID NO:49). In some embodiments, the $V_H$ CDR3 is NRGDIYYDFTYAMDI (SEQ ID NO:50). In some embodiments, the $V_H$ CDR3 is NRGDIYYDFTYAMDQ (SEQ ID NO:51). In some embodiments, the $V_H$ CDR3 is NRGDIYYDFTYAMDY (SEQ ID NO:52). In some embodiments, the $V_H$ CDR3 is NRGDIYYDFTYAMDS (SEQ ID NO:53). In some embodiments, the antibody comprises a $V_H$ region set forth in FIG. 4 and a $V_L$ region set forth in FIG. 5.

In some embodiments, an anti-PcrV antibody administered in accordance with the treatment methods of the invention is a Fab or whole immunoglobulin molecule. In some embodiments, the antibody is PEGylated.

BRIEF DESCRIPTION OF THE DRAWINGS

FIG. 1 provides data showing the reduction in *Staphylococcus aureus* levels in the sputum of CF patients at day 14 following treatment with placebo, 3 mg of an anti-PcrV antibody (3 mg Ab), or 10 mg of an anti-PcrV antibody (10 mg Ab).

FIG. 2 provides data showing the reduction in *Staphylococcus aureus* levels in the sputum of CF patients at day 28 following treatment with placebo, 3 mg of an anti-PcrV antibody (3 mg Ab), or 10 mg of an anti-PcrV antibody (10 mg Ab).

FIG. 3 provides data showing the reduction in *Staphylococcus aureus* levels in the sputum of CF patients at day 56 following treatment with placebo, 3 mg of an anti-PcrV antibody (3 mg Ab), or 10 mg of an anti-PcrV antibody (10 mg Ab).

FIG. 4 shows sequences of exemplary $V_H$ regions of anti-PcrV antibodies for use in the invention. CDR sequences are underlined. The VH1 sequence (SEQ ID NO:1) is aligned to human germ-line sequence VH1-18 (SEQ ID NO:31). VH3-subclass antibodies (SEQ ID NOS:7, 9, 5, 11, 3, 19, 27, 29, 13, 15, 17, 21 and 23, 25, 26 and 35, respectively) are shown aligned to human germ-line sequence VH3-30.3 (SEQ ID NO:33). J-segments are aligned to either human germ-line JH3 or JH6 (SEQ ID NO:38). The $V_H$-segments depicted in FIG. 4 correspond to the sequence up to the CDR3 sequence.

FIG. 5 shows sequences of exemplary $V_L$ regions of anti-PcrV antibodies for use in the invention. CDR sequences are underlined. Vkappa-subclass antibodies (SEQ ID NOS:24, 2, 8, 10, 14, 6, 4, 12, 37, 36 and 43, 18, 20 and 22, respectively) are shown aligned to human germline sequences VKI L12 (SEQ ID NO:39) or VKIII L2 (SEQ ID NO:40). J-segments are aligned to human germ-line JK2. Vlambda-subclass antibodies (SEQ ID NOS:30, 32 and 44 and 28, respectively) are shown aligned to human germline sequences VL3 31 (SEQ ID NO:41) or VL2 2c (SEQ ID NO:42). J-segments are aligned to human germ-line JL2.

DETAILED DESCRIPTION OF THE INVENTION

As used herein, a "low level" of *Pseudomonas* in patients infected with both *Pseudomonas aeruginosa* and *Staphylococcus aureus* refers to a *Pseudomonas* level that would not be treated with antibiotics. Thus, the level of *Pseudomonas* is less than the level of *Staphylococcus*, i.e., in a standard colony forming unit (cfu) quantification, the *Pseudomonas* colony forming units/ml (cfu/ml) are about 20% or less of the *Staphylococcus* cfu/ml. In CF patients with a chronic *P. aeruginosa* infection, the TTSS-expressing *P. aeruginosa* bacteria are often less than about 10%, or less than about 1%, of the total *P. aeruginosa* burden measured in the sputum. A "low level of TTSS-expressing *Pseudomonas*" in a patient, such as a CF patient, infected with both *Pseudomonas aeruginosa* and *Staphylococcus aureus* refers to a level at which the level of TTSS-expressing *Pseudomonas* is about 10% or less, typically about 5% or 1% or less, of the level of *Staphylococcus*. Thus, the TTSS-expressing *Pseudomonas* cfu are about 10% or less than the *Staphylococcus* cfu. In some embodiments, e.g., in a mechanically ventilated patient, a low-level of *Pseudomonas aeruginosa* is less than about $10^3$ cfu/ml in an endotracheal aspirate (ETA) sample (e.g., Louis, et al., *The Journal of Trauma: Injury, Infection, and Critical Care* 66:1052-1059, 2009). In some embodiments, a low-level of *Pseudomonas aeruginosa* is less than about $10^2$ cfu/ml in a bronchoalveolar lavage (BAL) sample. In some embodiments, e.g., in a cystic fibrosis patient, a low level of *Pseudomonas aeruginosa* is less than about $10^5$ cfu/g of sputum, where the proportion of TTSS-expressing *Pseudomonas aeruginosa* is 10% or less, of the total *Pseudomonas aeruginosa* bacteria. A burn patient or neutorpenic cancer patient treated in accordance with the methods of the invention has a titer of $10^3$ cfu/g *Staphylococcus aureus* to $10^2$ cfu/g tissue *Pseudomonas aeruginosa* (e.g., Hendricks et al., *J. Bone & Joint Surgery* 83:855-861, 2001).

An "acute" infection, such as an "acute" *Staphylococcus aureus* infection, refers to an infection in which the level of infectious agent is sufficient to warrant treatment, e.g., greater than $10^3$ cfu/ml in ETA in a mechanically ventilated patient, greater than $10^2$ cfu/ml in a BAL, greater than about $10^5$ cfu/g of sputum in a cystic fibrosis patient, or in a wound, greater than $10^3$ cfu/g biopsy or exudate. In the context of this invention, the term "acute" refers not only to a sudden onset infection, but also encompasses a chronic infection where the level of infectious agent, e.g., *S. aureus*, increases to an amount that warrants treatment, i.e., exacerbation of a chronic infection. The term "acute *S. aureus* infection" is used synonymously with "high level *S. aureus*" infection. Thus, a patient having a *Staphylococcus aureus* infection with a low level of *Pseudomonas aeruginosa* that is treated with a PcrV antagonist in accordance with the invention has a "high level" of *S. aureus* if it is determined that the patient needs to be treated for the *S. aureus* infection.

As used herein, an "antibody" refers to a protein functionally defined as a binding protein and structurally defined as comprising an amino acid sequence that is recognized by one of skill as being derived from the framework region of an immunoglobulin-encoding gene of an animal that produces antibodies. An antibody can consist of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains, respectively.

The term antibody as used herein includes antibody fragments that retain binding specificity. For example, there are a number of well characterized antibody fragments. Thus, for example, pepsin digests an antibody C-terminal to the disulfide linkages in the hinge region to produce F(ab)'$_2$, a dimer of Fab which itself is a light chain joined to VH-CH1 (Fd) by a disulfide bond. The F(ab)'$_2$ may be reduced under mild conditions to break the disulfide linkage in the hinge region thereby converting the (Fab')$_2$ dimer into an Fab' monomer. The Fab' monomer is essentially a Fab with all or part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that fragments can be synthesized de novo either chemically or by utilizing recombinant DNA methodology. Thus, the term "antibody" also includes antibody fragments produced either by the modification of whole antibodies or synthesized using recombinant DNA methodologies.

Antibodies of the invention include dimers such as $V_H$-$V_L$ dimers, $V_H$ dimers, or $V_L$ dimers, including single chain antibodies (antibodies that exist as a single polypeptide chain), such as single chain Fv antibodies (sFv or scFv) in which a variable heavy and a variable light region are joined together (directly or through a peptide linker) to form a continuous polypeptide. The single chain Fv antibody is a covalently linked $V_H$-$V_L$ heterodimer which may be expressed from a nucleic acid including $V_H$- and $V_L$-encoding sequences either joined directly or joined by a peptide-encoding linker (e.g., Huston, et al. *Proc. Nat. Acad. Sci. USA,* 85:5879-5883, 1988). While the $V_H$ and $V_L$ are connected to each as a single polypeptide chain, the $V_H$ and $V_L$ domains associate non-covalently. Alternatively, the antibody can be another fragment, such as a disulfide-stabilized Fv (dsFv). Other fragments can also be generated, including using recombinant techniques. The scFv antibodies and a number of other structures converting the naturally aggregated, but chemically separated light and heavy polypeptide chains from an antibody V region into a molecule that folds into a three dimensional structure substantially similar to the structure of an antigen-binding site are known to those of skill in the art (see e.g., U.S. Pat. Nos. 5,091,513, 5,132,405, and 4,956,778). In some embodiments, antibodies include those that have been displayed on phage or generated by recombinant technology using vectors where the chains are secreted as soluble proteins, e.g., scFv, Fv, Fab, (Fab')$_2$ or generated by recombinant technology using vectors where the chains are secreted as soluble proteins. Antibodies for use in the invention can also include diantibodies and miniantibodies. Further, antibodies of the invention include heavy chain dimers, such as antibodies from camelids. Since the $V_H$ region of a heavy chain dimer IgG in a camelid does not have to make hydrophobic interactions with a light chain, the region in the heavy chain that normally contacts a light chain is changed to hydrophilic amino acid residues in a camelid. $V_H$ domains of heavy-chain dimer IgGs are called VHH domains. Antibodies of the invention include single domain antibodies (dAbs) and nanobodies (see, e.g., Cortez-Retamozo, et al., *Cancer Res.* 64:2853-2857, 2004).

As used herein, "V-region" refers to an antibody variable region domain comprising the segments of Framework 1, CDR1, Framework 2, CDR2, and Framework 3, including CDR3 and Framework 4, which segments are added to the V-segment as a consequence of rearrangement of the heavy chain and light chain V-region genes during B-cell differentiation. A "V-segment" as used herein refers to the region of the V-region (heavy or light chain) that is encoded by a V gene. The V-segment of the heavy chain variable region encodes FR1—CDR1-FR2-CDR2 and FR3. For the purposes of this invention, the V-segment of the light chain variable region is defined as extending though FR3 up to CDR3.

As used herein, the term "J-segment" refers to a subsequence of the encoded variable region comprising a C-terminal portion of a CDR3 and the FR4. An endogenous J-segment is encoded by an immunoglobulin J-gene.

As used herein, "complementarity-determining regions (CDRs)" refers to the three hypervariable regions in each chain that interrupt the four "framework" regions established by the light and heavy chain variable regions. The CDRs are primarily responsible for binding to an epitope of an antigen. The CDRs of each chain are referred to as CDR1, CDR2, and CDR3, numbered sequentially starting from the N-terminus, and are also identified by the chain in which the particular CDR is located. Thus, for example, a $V_H$ CDR3 is located in the variable domain of the heavy chain of an antibody in which it is found, whereas a $V_L$ CDR1 is the CDR1 from the variable domain of the light chain of an antibody in which it is found.

The sequences of the framework regions of different light or heavy chains are relatively conserved within a species. The framework region of an antibody, that is the combined framework regions of the constituent light and heavy chains, serves to position and align the CDRs in three dimensional space.

The amino acid sequences of the CDRs and framework regions can be determined using various well known definitions in the art, e.g., Kabat, Chothia, international ImMunoGeneTics database (IMGT), and AbM (see, e.g., Johnson et al., supra; Chothia & Lesk, 1987, Canonical structures for the hypervariable regions of immunoglobulins. *J. Mol. Biol.* 196, 901-917; Chothia C. et al., 1989, Conformations of immunoglobulin hypervariable regions. Nature 342, 877-883; Chothia C. et al., 1992, structural repertoire of the human VH segments J. Mol. Biol. 227, 799-817; Al-Lazikani et al., *J. Mol. Biol.* 1997, 273(4)). Definitions of antigen combining sites are also described in the following: Ruiz et al., IMGT, the international ImMunoGeneTics database. *Nucleic Acids Res.,* 28, 219-221 (2000); and Lefranc, M.-P. IMGT, the international ImMunoGeneTics database. *Nucleic Acids Res.* Jan 1; 29(1):207-9 (2001); MacCallum et al, Antibody-antigen interactions: Contact analysis and binding site topography, *J. Mol. Biol.,* 262 (5), 732-745 (1996); and Martin et al, *Proc. Natl. Acad. Sci.* USA, 86, 9268-9272 (1989); Martin, et al, *Methods Enzymol.,* 203, 121-153, (1991); Pedersen et al, *Immunomethods,* 1, 126, (1992); and Rees et al, In Sternberg M. J. E. (ed.), Protein Structure Prediction. Oxford University Press, Oxford, 141-172 1996).

"Epitope" or "antigenic determinant" refers to a site on an antigen to which an antibody binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed (1996).

The term "minimal essential binding specificity determinant" or "MEBSD" as used in the context of the current invention refers to the minimum contiguous or non-contiguous amino acid sequence within a CDR region necessary for determining the binding specificity of an antibody. Often, the minimum binding specificity determinants reside within a portion or the full-length of the CDR3 sequences of the heavy and light chains of the antibody.

As used herein, the terms "PcrV antagonizing antibody" or an "anti-PcrV antibody antagonist of the *Pseudomonas aeruginosa* Type III secretion system" are used interchangeably to refer to an antibody that binds to PcrV and inhibits the Type III secretion system. Inhibition occurs when secretion through the Type III secretion system is at least about 10% less, for example, at least about 25%, 50%, 75% less, or totally inhibited, in comparison to secretion when not exposed to the antibody antagonist. The terms "anti-PcrV antibody" and "PcrV antibody" are used synonymously unless otherwise stated.

An "antagonist of the PcrV Type III secretion system" or "TTSS antagonist" in the context of this invention refers to an agents that inhibits secretion through the TTSS by at least 10%, typically at least 25%, 50%, 75%, in comparison to secretion when not exposed to the antagonist.

The term "equilibrium dissociation constant ($K_D$) refers to the dissociation rate constant ($k_d$, time$^{-1}$) divided by the association rate constant ($k_a$, time$_{-1}$, M$^{-1}$). Equilibrium dissociation constants can be measured using any known method in the art. The antibodies used in the methods of the present invention are high affinity antibodies. Such antibodies have an affinity better than 500 nM, and often better than 50 nM or 10 nM. Thus, in some embodiments, the antibodies of the invention have an affinity in the range of 500 nM to 100 pM, or in the range of 50 or 25 nM to 100 pM, or in the range of 50 or 25 nM to 50 pM, or in the range of 50 nM or 25 nM to 1 pM.

As used herein, "humanized antibody" refers to an immunoglobulin molecule in which CDRs from a donor antibody are grafted onto human framework sequences. Humanized antibodies may also comprise residues of donor origin in the framework sequences. A humanized antibody can also comprise at least a portion of a human immunoglobulin constant region. Humanized antibodies may also comprise residues which are found neither in the recipient antibody nor in the imported CDR or framework sequences. Humanization can be performed using methods known in the art (e.g., Jones et al., *Nature* 321:522-525; 1986; Riechmann et al., *Nature* 332:323-327, 1988; Verhoeyen et al., *Science* 239:1534-1536, 1988); Presta, *Curr. Op. Struct. Biol.* 2:593-596, 1992; U.S. Pat. No. 4,816,567), including techniques such as "superhumanizing" antibodies (Tan et al., *J. Immunol.* 169: 1119, 2002) and "resurfacing" (e.g., Staelens et al., *Mol. Immunol.* 43: 1243, 2006; and Roguska et al., *Proc. Natl. Acad. Sci USA* 91: 969, 1994).

A "Humaneered™" antibody in the context of this invention refers to an engineered human antibody having a binding specificity of a reference antibody. A "Humaneered™" antibody for use in this invention has an immunoglobulin molecule that contains minimal sequence derived from a donor immunoglobulin. Typically, an antibody is "Humaneered™" by joining a DNA sequence encoding a binding specificity determinant (BSD) from the CDR3 region of the heavy chain of the reference antibody to human $V_H$ segment sequence and a light chain CDR3 BSD from the reference antibody to a human $V_L$ segment sequence. A "BSD" refers to a CDR3-FR4 region, or a portion of this region that mediates binding specificity. A binding specificity determinant therefore can be a CDR3-FR4, a CDR3, a minimal essential binding specificity determinant of a CDR3 (which refers to any region smaller than the CDR3 that confers binding specificity when present in the V region of an antibody), the D segment (with regard to a heavy chain region), or other regions of CDR3-FR4 that confer the binding specificity of a reference antibody. Methods for humaneering are provided in US patent application publication no. 20050255552 and US patent application publication no. 20060134098.

The term "hybrid" when used with reference to portions of a nucleic acid or protein, indicates that the nucleic acid or protein comprises two or more subsequences that are not normally found in the same relationship to each other in nature. For instance, a "hybrid" nucleic acid is often recombinantly produced, having two or more sequences, e.g., from unrelated genes, arranged to make a new functional nucleic acid. Similarly, a "hybrid" protein refers to two or more subsequences that are not normally found in the same relationship to each other in nature.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, e.g., recombinant cells express genes that are not found within the native (non-recombinant) form of the cell or express native genes that are otherwise abnormally expressed, under expressed or not expressed at all. By the term "recombinant nucleic acid" herein is meant nucleic acid, originally formed in vitro, in general, by the manipulation of nucleic acid, e.g., using polymerases and endonucleases, in a form not normally found in nature. In this manner, operably linkage of different sequences is achieved. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. Similarly, a "recombinant protein" is a protein made using recombinant techniques, i.e., through the expression of a recombinant nucleic acid as depicted above.

The phrase "specifically (or selectively) binds" to a protein or peptide or "specifically (or selectively) immunoreactive with," when referring to a protein or peptide, refers to a binding reaction where the antibody binds to the protein of interest. In the context of this invention, the antibody typically binds to PcrV with an affinity of 500 nM or less, and has an affinity of 5000 nM or greater, for other antigens.

The terms "identical" or percent "identity," in the context of two or more polypeptide (or nucleic acid) sequences, refer to two or more sequences or subsequences that are the same or have a specified percentage of amino acid residues (or nucleotides) that are the same (i.e., about 60% identity, preferably 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site). Such sequences are then said to be "substantially identical." "Substantially identical" sequences also includes sequences that have deletions and/or additions, as well as those that have substitutions, as well as naturally occurring, e.g., polymorphic or allelic variants, and man-made variants. As described below, the preferred algorithms can account for gaps and the like. Preferably, protein sequence identity exists over a region that is at least about 25 amino acids in length, or more preferably over a region that is 50-100 amino acids in length, or over the length of a protein.

A "comparison window", as used herein, includes reference to a segment of one of the number of contiguous positions selected from the group consisting typically of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

Preferred examples of algorithms that are suitable for determining percent sequence identity and sequence similarity include the BLAST and BLAST 2.0 algorithms, which are described in Altschul et al., *Nuc. Acids Res.* 25:3389-3402 (1977) and Altschul et al., *J. Mol. Biol.* 215:403-410 (1990). BLAST and BLAST 2.0 are used, with the parameters described herein, to determine percent sequence identity for the nucleic acids and proteins of the invention. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. The term "purified" in some embodiments denotes that a protein gives rise to essentially one band in an electrophoretic gel. Preferably, it means that the protein is at least 85% pure, more preferably at least 95% pure, and most preferably at least 99% pure.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated, e.g., naturally contiguous, sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, often silent variations of a nucleic acid which encodes a polypeptide is implicit in a described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables and substitution matrices such as BLOSUM providing functionally similar amino acids are well known in the art. Such conservatively modified variants are in addition to and do not exclude polymorphic variants, interspecies homologs, and alleles of the invention. Typical conservative substitutions for one another include: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

INTRODUCTION

The present invention is based on the surprising discovery that a PcrV antibody that antagonizes the *P. aeruginosa* Type III secretion system can be used for the treatment of infections where the patient has a low level of *P. aeruginosa* and levels of *Staphylococcus aureus* that warrant treatment, i.e., "high" levels of *Staphylococcus aureus*.

Staphylococcus aureus

*Staphylococcus aureus* is a gram positive bacterium that is considered the most virulent of the staphylococcal species. *S. aureus* is distinguished from the other staphylococcal species by the presence of coagulase and Protein A and can be readily diagnosed by standard microbiological tests. *S. aureus* causes disease through both toxin-mediated and non-toxin-mediated mechanisms.

*Staphylococcus aureus* is present, primarily on the skin, of up to 50% of healthy humans. Colonization is higher in certain groups of people, such as insulin-dependent diabetics, HIV-infected individuals, patients undergoing hemodialysis and persons with skin damage, such as eczema, as well as injection drug users. In addition neutropenic individuals (e.g., who have undergone chemotherapy or radiation therapy), as well as persons having certain congenital deficiencies in cellular immunity, are at increased risk for infection. *S. aureus* is also recognized as a cause of primary bacteremia, and is also found in skin and soft tissue infections, respiratory infections and, at times, infective endocarditis.

*Staphylococcus aureus* is a leading cause of nosocomial infections and surgical wound infections, which are increasingly resistant to known antibiotics.

Common sites of staphylococcal colonization leading to infection in humans are the anterior nares of the nose. These organisms are also capable of foaming biofilms, particularly on prosthetic devices and catheters.

Bacteremia is the presence of viable bacteria in the blood, and can be diagnosed by blood cultures. If left unchecked, it can progress to sepsis and endocarditis, which are characterized by a host immune response to the invading bacteria and can be lethal. Clinically, sepsis is characterized by respiratory alkalosis, fever and hypotension.

Most strains of *Staphylococcus*, including *S. aureus*, are now resistant to penicillins. Among the small proportion (est. <5%) that are sensitive, penicillinase-resistant penicillins, such as oxacillin and nafcillin, are commonly used to treat patients that have a *Staphylococcus aureus* infection. Cephalosporins may also be used to treat *S. aureus* infections. Carbapenems, such as imipenem, are not considered useful for methicillin-resistant *Staphylococcus aureus* (MRSA), although they can be used successfully for methicillin-sensitive strains (MSSA).

Vancomycin is often used for the treatment of methicillin-resistant *staphylococcus* infections, including MRSA. Another drug, daptomycin is a lipopeptide that, like vancomycin, is specific for gram positive bacteria. It has been used with some success against MRSA and vancomycin-partially resistant *S. aureus*. (see, Moise et al. *Lancet Inf.* 9:617-624, 2009)

Other antibiotics that may be used to treat *S. aureus* include quinolones, particularly fluoroquinolones, chloramphenicol, linezolid (an oxazolidinone), minocycline, quinupristin/dalfopristin (Q/D) and trimethoprim-sulfomethoxazole (TMP-SMX); however, many of these are bacteriostatic against staphylococci, and have less overall anti-staphylococcal activity. Combinations of antimicrobial agents have also been used successfully to treat *S. aureus* infections include: these include: rifampin+aminoglycoside (gentamicin)+fusidic acid; β-lactams+aminoglycosides; vancomycin+gentamicin; vancomycin+rifampin.

It is generally standard practice for staphylococcal infections to perform culture and sensitivity testing of the culture; although this can take several days. In those cases where culture is performed, certain treatment guidelines have been established in U.S. medical practice: For penicillin-sensitive staph infections, penicillin G, nafcillin, oxacillin, cefazolin or vancomycin can be used.

For methicillin-sensitive strains, nafcillin or oxicillin, alternatively cefazolin or vancomycin, can be used.

For methicillin-resistant strains, vancomycin is indicated, with alternatives: TMP-SMX, minocycline, ciprofloxacin, levofloxacin, Q/D; linezolid or daptomycin for skin infections.

For MRSA with partial or complete vancomycin resistance: vancomycin+an aminoglycoside. (see, e.g., Kasper, D. L, et al, eds: Harrison's Principles of Internal Medicine, 16th Ed., McGraw-Hill, 2005.)

Pseudomonas aeruginosa

*P. aeruginosa* is a gram negative bacterium that is identified in culture using standard clinical laboratory techniques, e.g., differential culture on agar. It is widespread in nature; however, many infections are acquired in the hospital setting. It is a common cause of pneumonia in the intensive care unit, particularly in patients maintained on mechanical ventilators, Infections usually begin with colonization, preferably in moist environments, such as cutaneous or mucosal surfaces.

*P. aeruginosa* often progresses in immunocompromised patients, such as neutropenic patients, where it can result in bacteremia and septic shock. Other common sites of infection include the urinary and gastrointestinal tracts, lungs, skin and soft tissues, as well as indwelling venous catheters; infections may also occur in the central nervous system, ear, eye, bones and joints. It forms biofilms, particularly on prostheses, such as heart valves (which may result in endocarditis). Burn patients are also often susceptible to *P. aeruginosa* infection.

Treatment of *P. aeruginosa* infection depends upon the location, type and severity of the infection. In some cases, combination therapy is appropriate. In cystic fibrosis, for example, where many patients have chronic infections, intermittent therapy with inhaled tobramycin has been shown to reduce exacerbations. Resistance of the microbe to certain antibiotics has been reported, however.

The following is a list of antibiotics that may be used to treat *Pseudomonas aeruginosa*:
Penicillins (piperacillin, piperacillin/tazobactam, mezlocillin, ticarcillin, ticarcillin/clavulanate),
Cephalosporins (Ceftazidime, cefoperazone, cefepime),
Carbapenems (imipenem/cilastatin; meropenem),
Monobactams (aztreonam),
Aminoglycosides (tobramycin, gentamicin, amikacin),
Fluoroquinolones (ciprofloxacin, levofloxacin), and
Other (polymyxin B, Colistin)
Common treatment regimens include:
Bacteremia: penicillin+aminoglycoside; penicillin+ciprofloxacin; cephalosporin, aztreonam or carbapenem+aminoglycoside or ciprofloxacin;
CNS: ceftazidime, optionally plus aminoglycoside; cefepime; ciprofloxacin; aztreonam; meropenem;
Bone/Joint: penicillin+(aminoglycoside or ciprofloxacin); cephalosporin; aztreonam; fluoroquinolone; carbapenem;

External otitis: cephalosporin; carbapenem; ciprofloxacin; cephalosporin+aminoglycoside;

Keratinitis/corneal ulcer (eye): tobramycin (topical), optionally with piperacillin or ticarcillin (topical); ciprofloxacin or ofloxacin (topical); and Urinary tract: ciprofloxacin; aminoglycoside; penicillin; cephalosporin; carbapenen. (See, e.g., Kasper, D. L, et al, eds: Harrison's Principles of Internal Medicine, 16th Ed., McGraw-Hill, 2005).

In the current invention, a PcrV antagonist, e.g., an anti-PcrV antibody described herein, is administered to a patient that has an acute *S. aureus* infection. In some embodiments, the *S. aureus*-infected patient also receives antibiotic therapy, either concurrently, or before or after treatment with the anti-PcrV antibody. The antibiotic therapy involves use of antibiotics commonly used to treat *S. aureus* infections. In some embodiments, the patient is treated with an antibiotic that is selective for gram positive organisms. In some embodiments, the patient is treated with an anti-PcrV antibody and vancomycin or daptomycin. In some embodiments, the patient is treated with an antibiotic that is not used to treat *Pseudomonas* infection. In some embodiments, the patient is treated with a PcrV antagonist, e.g., an anti-PcrV antibody antagonist and an antibiotic with the proviso that the antibiotic is not an aminoglycoside, e.g., tobramycin.

Methods of Treating a Patient

The invention provides methods of treating a patient that has a *Staphylococcus aureus* infection that warrants treatment and a low level of *P. aeruginosa*, the method comprising administering an antagonist of the *P. aeruginosa* TTSS.

In typical embodiments, the antagonist is a PcrV antibody antagonist. In some embodiments, the patient being treated has cystic fibrosis, ventilator-associated pneumonia (VAP), is a neutropenic cancer patient or is a burn patient. A patient that is a candidate for treatment in accordance with the methods of the invention, typically has *P. aeruginosa* levels that are less than about $10^3$/cfu/ml in an endotracheal aspirate (in a mechanically ventilated patient) or less than about $10^2$ cfu/ml in a bronchoalveolar lavage or, in a CF patient, less than about $10^5$/g sputum. In CF patients with a chronic *P. aeruginosa* infection the TTSS-expressing *P. aeruginosa* bacteria are typically less than 10% of the total *P. aeruginosa* burden measured in the sputum. Other patients, e.g., neutropenic patients, burn patients and the like, who are infected with *Staphylococcus aureus* and who also have a low level of *Pseudomonas aeruginosa* where the patient warrants treatment for the *Staphylococcus aureus* infection can also be treated with a selective PcrV antagonist, e.g., an anti-PcrV antibody.

The methods of the invention comprise administering an anti-PcrV antibody as a pharmaceutical composition to a *Staphylococcus*-infected patient in a therapeutically effective amount using a dosing regimen suitable for treatment of the *Staphylococcus* infection. The antibody composition can be formulated for use in a variety of drug delivery systems.

The PcrV antibody is provided in a solution suitable for injection into the patient such as a sterile isotonic aqueous solution for injection. One or more physiologically acceptable excipients or carriers can also be included in the compositions for proper formulation. Suitable formulations for use in the present invention are found in *Remington: The Science and Practice of Pharmacy,* 21st Edition, Philadelphia, Pa. Lippincott Williams & Wilkins, 2005.

The antibody is dissolved or suspended at a suitable concentration in an acceptable carrier. In some embodiments the carrier is aqueous, e.g., water, saline, phosphate buffered saline, and the like. The compositions may contain auxiliary pharmaceutical substances as required to approximate physiological conditions, such as pH adjusting and buffering agents, tonicity adjusting agents, and the like.

An anti-PcrV antibody is administered to a patient having a *Staphylococcus* infection in an amount sufficient to cure or at least partially reduce the level of *Staphylococcus* in the patient. An amount adequate to accomplish this is defined as a "therapeutically effective dose." A therapeutically effective dose is determined by monitoring a patient's response to therapy. Typical benchmarks indicative of a therapeutically effective dose include amelioration of symptoms of infection in the patient, e.g., a reduction of fever, or a decrease in the levels of *Staphylococcus aureus* in the patient. Amounts effective for this use will depend upon the severity of the disease and the general state of the patient's health, including other factors such as age, weight, gender, administration route, etc. Single or multiple administrations of the antibody and antibiotic may be administered depending on the dosage and frequency as required and tolerated by the patient. In any event, the methods provide a sufficient quantity of PcrV antibody and antibiotic to effectively treat the patient.

In some embodiments, the antibody is administered to the patient in combination with an antibiotic commonly used to treat *Staphylococcus aureus* infections, particularly where the antibiotic is not fully effective against the *Staphylococcus aureus* that has infected the patient, or the *Staph. aureus* has some resistance to the antibiotic, e.g., reduced susceptibility to vancomycin. The antibiotic can be administered concurrently with the antibody or before or after treatment with the antibody. In some embodiments, the antibiotic is vancomycin or daptomycin.

The Type III secretion system antagonist, e.g., an anti-PcrV antibody, may also be administered in combination with other therapies to treat the *Staphylococcus* infection.

In combination treatments, the anti-PcrV antibody can be administered before or after the other agents, e.g., within the same day, or within the same week, or at the same time. In some embodiments, the antagonist is administered concurrently with the agent after one or more initial treatments with the agents, e.g., an antibiotic, alone.

The anti-PcrV antibody can be administered by injection or infusion through any suitable route including but not limited to intravenous, subcutaneous, intramuscular, intratracheal, or intraperitoneal routes. In some embodiments, the antibody is administered by insufflation. In an exemplary embodiment, the antibody may, e.g., be stored at 10 mg/ml in sterile isotonic aqueous saline solution for injection at 2-8° C. and is diluted in either 100 ml or 200 ml 0.9% saline for injection prior to administration to the patient. The antibody is administered by intravenous infusion over the course of 1 hour at a dose of between 0.2 and 10 mg/kg. In other embodiments, the antibody is administered by intravenous infusion over a period of between 15 minutes and 2 hours. In still other embodiments, the administration procedure is via sub-cutaneous bolus injection.

The dose of TTSS antagonist is chosen in order to provide effective therapy for the patient. For an anti-PcrV antibody, often the dose is in the range of less than 0.1 mg/kg body weight to 25 mg/kg body weight or in the range 1 mg-2 g per patient. Preferably the dose is in the range 1-10 mg/kg or approximately 50 mg-1000 mg/patient. The dose may be repeated at an appropriate frequency, e.g., which may be in the range of once per day to once a week, depending on the pharmacokinetics of the antibody (e.g. half-life of the antibody in the circulation) and the pharmacodynamic response (e.g. the duration of the therapeutic effect of the antibody). In some embodiments, the antibody has an in vivo half-life of between about 7 and about 25 days and antibody dosing is repeated once per week.

In further embodiments, the antibody is PEGylated. For example, an antibody of the invention may be PEGylated, e.g., using methods as described herein, and administered to a patient infected with *P. aeruginosa*

Antibiotics

In some embodiments, the antibody is administered in combination with an antibiotic to treat the *Staphylococcus aureus* infection.

In some embodiments, the methods of treating the *Staphylococcus aureus* infection comprise administering an anti-PcrV antibody in conjunction with an antibiotic such as a penicillin, e.g., nafcillin, oxacillin, flucoxacillin, ticarcillin, dicloxacillin, azlocillin, penicillin, or pipericillin. As understood in the art a ureidopenicillin antibiotic such as piperacillin, is typically administered in a format that includes a penicillinase inhibitor such as tazobactam. Other antibiotics that can be used include macrolides, cephalosporins. For treatment of MRSA infections, antibiotics used include quinolones, clindamycin (a lincosamide), quinupristin/dalfopristin, co-trimoxazole (also commonly known as trimethoprim/sulfamethoxazole), linezolid, and glycopeptides such as vancomycin, telavancin, and teicoplanin; a lipopeptide such as daptomycin, chloramphenicol, rifampicin, doxycyclin, minocycline, glycylcyclines such as tigecycline, quinupristin/dalfopristin (Q/D) and trimethoprim-sulfomethoxazole (TMP-SMX) as well as combinations of antibiotics known in the art (see, e.g., the Introduction section).

Methods of administering antibiotics are well known in the art. For example, the antibiotic is typically administered orally or by injection, for example, intravenously, subcutaneously, intramuscularly, parenterally, intratracheally or using spinal or epidermal routes. In some embodiments the antibiotic can be aerosolized for administration by inhalation.

Anti-PcrV Antibodies

The invention relates to methods of treatment of *Staphylococcus aureus* infections using a functional antagonists of the Type III secretion system. This section provides examples of antibodies, e.g., engineered antibodies, that can be employed in the therapeutic regimens of the invention.

Antibodies for use in the invention typically comprise variable regions with a high degree of homology to human germline $V_H$ and $V_L$ sequences. The CDR3 sequences of the heavy and light chains comprise a pair of binding specificity determinants (BSD) from the monoclonal anti-PcrV antibody Mab 166 (Frank et al., *J. Infectious Dis.* 186: 64-73, 2002; and U.S. Pat. No. 6,827,935) and the antibodies of the invention compete with Mab166 for binding to a neutralizing epitope on the PcrV protein (see, e.g., U.S. Pat. No. 6,827,935).

In some embodiments, antibodies for use in the invention have a minimal essential binding specificity determinant in CDRH3 that has the amino acid sequence NRGDIYYDFTY (SEQ IDN NO:54). In some embodiments, such an antibody has a heavy chain CDR3 sequence NRGDIYYDFTYA(M/F)DX (SEQ ID NO:55), where X is I, S, or Q.

In some embodiments, antibodies for use in the invention have a minimal essential binding specificity determinant in CDRL3 that has the amino acid FWXTP (where X may be either S or G). Complete V-regions are generated in which the BSD forms part of the CDR3 and additional sequences are used to complete the CDR3 and add a FR4 sequence. Typically, the portion of the CDR3 excluding the BSD and the complete FR4 are comprised of human germ-line sequences. In preferred embodiments, the CDR3-FR4 sequence excluding the BSD differs from human germ-line sequences by not more than 2 amino acids on each chain.

The human germline V-segment repertoire consists of 51 heavy chain V-segments, 40 κ light chain V-segments, and 31λ light chain V-segments, making a total of 3,621 germline V-region pairs. In addition, there are stable allelic variants for most of these V-segments, but the contribution of these variants to the structural diversity of the germline repertoire is limited. The sequences of all human germ-line V-segment genes are known and can be accessed in the V-base database (on the worldwide web at vbase.mrc-cpe.cam.ac.uk), provided by the MRC Centre for Protein Engineering, Cambridge, United Kingdom (see, also Chothia et al., 1992, *J Mol Biol* 227:776-798; Tomlinson et al., 1995, *EMBO J.* 14:4628-4638; Cook et al. (1995) *Immunol. Today* 16: 237-242 and Williams et al., 1996, *J Mol Biol* 264:220-232); or the international ImMunoGeneTics database (IMGT). These sequences can be used as reference sources for the human germline segments in engineering antibodies for use in the invention.

Examples of high affinity, engineered antibodies that can be used in the invention are provided in U.S. application publication number 20090191186. Thus, an antibody for use in the invention can comprise a heavy chain and/or light chain of an anti-PcrV antibody described in WO/2009/073631. In some embodiments, the antibody has a heavy chain CDR3 that comprises NRGDIYYDFTYAMDX (SEQ ID NO:45), wherein X is I, Q, Y, or S; and a light chain CDR3 that comprises FW(S/G)TP (SEQ ID NO:46), e.g., a CDR3 having the sequence QQFWSTPYT (SEQ ID NO:47), QHFWGTPYT (SEQ ID NO:48), or QHFWSTPYT (SEQ ID NO:49). In some embodiments, such an antibody comprises $V_H$ region V-segment that has at least 90% identity, or at least 91%, 92% 93%, 94%, 95%, 965, 97%, 98%, 99%, or 100% identity to a V-segment sequence of a $V_L$ region shown in FIG. 5.

An antibody for use in any of the treatment methods of the invention may comprise any of the $V_H$ regions shown in FIG. 4 in combination with any of the $V_L$ regions shown in FIG. 5. Thus, in some embodiments, an antibody for use in the invention comprises a $V_H$ region of SEQ ID NO:1 and a $V_L$ region of SEQ ID NO:2; or a $V_H$ region of SEQ ID NO:3 and a $V_L$ region of SEQ ID NO:4; or a $V_H$ region of SEQ ID NO:5 and a $V_L$ region of SEQ ID NO:6; or a $V_H$ region of SEQ ID NO:7 and a $V_L$ region of SEQ ID NO:8; or a $V_H$ region of SEQ ID NO:11 and a $V_L$ region of SEQ ID NO:12; or a $V_H$ region of SEQ ID NO:9 and a $V_L$ region of SEQ ID NO:10; or a $V_H$ region of SEQ ID NO:13 and a $V_L$ region of SEQ ID NO:10; or a VH region of SEQ ID NO:13 and a $V_L$ region of SEQ ID NO:4; or a $V_H$ region of SEQ ID NO:13 and a $V_L$ region of SEQ ID NO:37; or a $V_H$ region of SEQ ID NO:21 and a $V_L$ region of SEQ ID NO:18; or a $V_H$ region of SEQ ID NO:17 and a $V_L$ region of SEQ ID NO:18; or a $V_H$ region of SEQ ID NO:26 and a $V_L$ region of SEQ ID NO:24; or a VH region of SEQ ID NO:25 and a $V_L$ region of SEQ ID NO:24; or a $V_H$ region of SEQ ID NO:23 and a $V_L$ region of SEQ ID NO:24; or a $V_H$ region of SEQ ID NO:35 and a $V_L$ region of SEQ ID NO:36; or $V_H$ region of SEQ ID NO:29 and a $V_L$ region of SEQ ID NO:20; or $V_H$ region of SEQ ID NO:29 and a $V_L$ region of SEQ ID NO:28; or a $V_H$ region of SEQ ID NO:29 and a $V_L$ region of SEQ ID NO:30; or a $V_H$ region of SEQ ID NO:29 and a $V_L$ region of SEQ ID NO:34; or a $V_H$ region of SEQ ID NO:3 and a $V_L$ region of SEQ ID NO:32.

An antibody that is employed in the invention can be in any format. For example, in some embodiments, the antibody can be an intact immunoglobulin including a complete constant region, e.g., a human constant region, or can be a fragment or derivative of an intact antibody, e.g., a Fab, Fab', F(ab')$_2$, scFv, Fv, or a single domain antibody, such as a nanobody or a camelid antibody.

Preparation of PcrV Antibodies

An anti-PcrV antibody used for treating a *S. aureus*-infected patient as described herein may be tested to confirm that the antibody retains the activity of antagonizing the Type III secretion system. The antagonist activity can be determined using any number of endpoints, including cytotoxicity assays. Exemplary assays are described, e.g., in U.S. Pat. No. 6,827,935. An antibody that is administered to treat the infection preferably retains at least 75%, preferably 80%, 90%, 95%, or 100%, of the Type III secretion pathway antagonist activity of Mab166 (U.S. Pat. No. 6,827,935).

A high-affinity antibody may be identified using well known assays to determine binding activity and affinity. Such techniques include ELISA assays as well as binding determinations that employ surface plasmon resonance or interferometry. For example, affinities can be determined by biolayer interferometry using a ForteBio (Mountain View, Calif.) Octet biosensor.

Antibodies for use in the methods of the invention may compete with Mab166 for binding to PcrV. The region of PcrV to which Mab166 binds has been identified (U.S. Pat. No. 6,827,935). PcrV or a fragment thereof that binds Mab166 can be employed in a competitive binding assay. The ability of an antibody to block or compete with Mab166 for binding to PcrV indicates that the antibody binds to the same epitope as Mab166 or to an epitope that is close to, e.g., overlapping, with the epitope that is bound by Mab166. In other embodiments an antibody described herein, e.g., an antibody comprising a $V_H$ and $V_L$ region combination as described above, can be used as a reference antibody for assessing whether another antibody competes for binding to PcrV. A test antibody is considered to competitively inhibit binding of a reference antibody, if binding of the reference antibody to the antigen is reduced by at least 30%, usually at least about 40%, 50%, 60% or 75%, and often by at least about 90%, in the presence of the test antibody. Many assays can be employed to assess binding, including ELISA, as well as other assays, such as immunoblots.

In typical embodiments, the antibodies used in the methods of the invention that antagonize the *P. aeruginosa* type III secretion system exhibit high affinity binding to PcrV. High affinity binding between an antibody and an antigen exists if the affinity of the antibody is less than 500 or 100 nM, for example, less than 50 nM or less than 25 nM, or less than 10 nM, or less than 1 nM, e.g., less than about 100 pM. The antibodies of the invention typically have an affinity of 50 nM or less, often 10 nM or less, when assayed as Fabs, e.g., using ELISA, surface plasmon resonance assays, or interferometry.

In some embodiments, an antibody employed for treating a *S. aureus*-infected patient population as described herein is more potent in a cellular cytotoxicity assay than Mab166.

Antibodies may be produced using any number of expression systems, including both prokaryotic and eukaryotic expression systems. Many such systems are widely available from commercial suppliers. In embodiments in which an antibody comprises both a $V_H$ and $V_L$ region, the $V_H$ and $V_L$ regions may be expressed using a single vector, e.g., in a dicistronic expression unit, or under the control of different promoters. In other embodiments, the $V_H$ and $V_L$ region may be expressed using separate vectors. The antibodies of the invention may be expressed with or without a methionine at the N-terminus. Thus, a $V_H$ or $V_L$ region as described herein may optionally comprise a methionine at the N-terminus.

An antibody used in the methods of the invention may be produced in any number of formats, including as a Fab, a Fab', a F(ab')$_2$, a scFv, or a dAB. An anti-PcrV antibody as described herein can also include a human constant region. The constant region of the light chain may be a human kappa or lambda constant region. The heavy chain constant region is often a gamma chain constant region, for example, a gamma-1, gamma-2, gamma-3, or gamma-4 constant region. In other embodiments, the antibody may be an IgA.

In some embodiments, the antibody is "non-immunogenic" when administered to a human. The term "non-immunogenic" as used here refers to a PcrV antibody that does not provoke antibody production against the anti-PcrV antibody when administered to a human. Antibodies can be assessed for immunogenicity using known assays, e.g., an electrochemiluminescence immunoassay. Such assays detect the level of antibodies present in a patient, e.g., in a serum sample from the patient, that react with the anti-PcrV antibody that is administered to the patient. An assay is considered to show that the antibody is non-immunogenic when no detectable antibody to the anti-PcrV antibody is present in the sample, e.g., in comparison to a control sample from an individual that was not administered the antibody.

PEGylation of Antibodies

In some embodiments, e.g., where the antibody is a fragment, the antibody can be conjugated to another molecule, e.g., polyethylene glycol (PEGylation) or serum albumin, to provide an extended half-life in vivo. Examples of PEGylation of antibody fragments are provided in Knight et al. *Platelets* 15:409, 2004 (for abciximab); Pedley et al., *Br. J. Cancer* 70:1126, 1994 (for an anti-CEA antibody); Chapman et al., *Nature Biotech.* 17:780, 1999; and Humphreys, et al., *Protein Eng. Des.* 20: 227, 2007).

In some embodiments, the anti-PcrV antibodies used to treat a *S. aureus* infection are in the form of a Fab' fragment. A full-length light chain is generated by fusion of a $V_L$-region to human kappa or lambda constant region. Either constant region may be used for any light chain; however, in typical embodiments, a kappa constant region is used in combination with a Vkappa variable region and a lambda constant region is used with a Vlambda variable region.

The heavy chain of the Fab' is a Fd fragment generated by fusion of a $V_H$-region of the invention to human heavy chain constant region sequences, the first constant (CH1) domain and hinge region. The heavy chain constant region sequences can be from any of the immunoglobulin classes, but is often from an IgG, and may be from an IgG1, IgG2, IgG3 or IgG4. Fab' antibodies for use in the invention may also be hybrid sequences, e.g., a hinge sequence may be from one immunoglobulin sub-class and the CH1 domain may be from a different sub-class. In a preferred embodiment, the heavy chain constant region including the CH1 domain and hinge sequence is from human IgG1.

In some embodiments, the Fab' molecule can be PEGylated. PEGylation methods are well known. For example, the antibody may be PEGylated at the hinge region, e.g., at cysteine residues that are suitable for conjugation to a polyethylene glycol derivative. Other methods of PEGylation, e.g., where the PEG is not introduced at a hinge, are also known. For example, Humphreys et al., supra, describe methods for PEGylation of cysteine residues outside the hinge region by disruption of the interchain disulphide bond between the heavy and light chain of a Fab.

Methods for purification of PEGylated Fab' and separation of the desired mono- or di-PEGylated Fab' from unreacted mPEG-maleimide and Fab' molecules containing higher numbers of PEG moieties are known in the art. Such methods include, for example, size-exclusion or ion-exchange chromatography.

Antibody Mimetics

Patients that have a low level of *P. aeruginosa* (less than about $10^4$/ml in endotracheal aspirate (ETA) in a mechanically ventilated patient, or less than about $10^2$/ml in bronchoalveolar lavage (BAL), or in a CF patient, less than about $10^5$/g sputum, and a *S. aureus* infection that warrants treatment may also be treated with a *P. aeruginosa* TTSS antagonist that is not an antibody. Thus, the TTSS antagonist may be an "antibody mimetic" that targets and binds to PcrV in a manner similar to antibodies. Certain of these "antibody mimics" use non-immunoglobulin protein scaffolds as alternative protein frameworks for the variable regions of antibodies. For example, Ku et al. (*Proc. Natl. Acad. Sci. U.S.A.* 92(14):6552-6556 (1995)) discloses an alternative to antibodies based on cytochrome b562 in which two of the loops of cytochrome b562 were randomized and selected for binding against bovine serum albumin. The individual mutants were found to bind selectively with BSA similarly with anti-BSA antibodies.

U.S. Pat. Nos. 6,818,418 and 7,115,396 disclose an antibody mimic featuring a fibronectin or fibronectin-like protein scaffold and at least one variable loop. Known as Adnectins, these fibronectin-based antibody mimics exhibit many of the same characteristics of natural or engineered antibodies, including high affinity and specificity for any targeted ligand. The structure of these fibronectin-based antibody mimics is similar to the structure of the variable region of the IgG heavy chain. Therefore, these mimics display antigen binding properties similar in nature and affinity to those of native antibodies. Further, these fibronectin-based antibody mimics exhibit certain benefits over antibodies and antibody fragments. For example, these antibody mimics do not rely on disulfide bonds for native fold stability, and are, therefore, stable under conditions which would normally break down antibodies. In addition, since the structure of these fibronectin-based antibody mimics is similar to that of the IgG heavy chain, the process for loop randomization and shuffling may be employed in vitro that is similar to the process of affinity maturation of antibodies in vivo.

Beste et al. (*Proc. Natl. Acad. Sci. U.S.A.* 96(5):1898-1903 (1999)) disclose an antibody mimic based on a lipocalin scaffold (Anticalin®). Lipocalins are composed of a β-barrel with four hypervariable loops at the terminus of the protein. The loops were subjected to random mutagenesis and selected for binding with, for example, fluorescein. Three variants exhibited specific binding with fluorescein, with one variant showing binding similar to that of an anti-fluorescein antibody. Further analysis revealed that all of the randomized positions are variable, indicating that Anticalin® would be suitable to be used as an alternative to antibodies. Thus, Anticalins® are small, single chain peptides, typically between 160 and 180 residues, which provides several advantages over antibodies, including decreased cost of production, increased stability in storage and decreased immunological reaction.

U.S. Pat. No. 5,770,380 discloses a synthetic antibody mimetic using the rigid, non-peptide organic scaffold of calixarene, attached with multiple variable peptide loops used as binding sites. The peptide loops all project from the same side geometrically from the calixarene, with respect to each other. Because of this geometric confirmation, all of the loops are available for binding, increasing the binding affinity to a ligand. However, in comparison to other antibody mimics, the calixarene-based antibody mimic does not consist exclusively of a peptide, and therefore it is less vulnerable to attack by protease enzymes. Neither does the scaffold consist purely of a peptide, DNA or RNA, meaning this antibody mimic is relatively stable in extreme environmental conditions and has a long life span. Further, since the calixarene-based antibody mimic is relatively small, it is less likely to produce an immunogenic response.

Murali et al. (*Cell Mol Biol* 49(2):209-216 (2003)) describe a methodology for reducing antibodies into smaller peptidomimetics, they term "antibody-like binding peptidomimetics" (ABiP) which may also be useful as an alternative to antibodies.

In addition to non-immunoglobulin protein frameworks, antibody properties have also been mimicked in compounds comprising RNA molecules and unnatural oligomers (e.g., protease inhibitors, benzodiazepines, purine derivatives and beta-turn mimics). Accordingly, non-antibody antagonists of TSSS can also include such compounds.

EXAMPLES

Example 1

Treatment of CF Patients with Anti-PcrV Antibody

CF patients were treated with a single intravenous injection of a humaneered antibody antagonist of the *P. aeruginosa* TSSS. Antibody was administered at a dose of either 3 mg/kg or 10 mg/kg on day 0. Bacterial counts were measured by taking induced sputum from patients at specified times following treatment plating out on agar plates. Colonies of *Staphylococcus aureus* (Sa) were counted after incubation for 24 hours at 30° C. FIGS. 1-3 show the reduction in *Staphylococcus aureus* levels in sputum samples taken at day 14, day 28, and day 56 following treatment with the anti-PcrV antibody. Treatment reduced the level of *Staphylococcus aureus* by as much as 3 logs.

Example 2

Treatment of Mechanically Ventilated Patients with Anti-PcrV Antibody

Mechanically ventilated patients with respiratory tract colonization with *Pseudomonas aeruginosa* (>$10^3$ cfu/ml but <$10^6$ cfu/ml ETA at day 0) were dosed I.V. at either 3 or 10 mg/kg of anti-PcrV antibody or with placebo. Patients were evaluated for 28 days following dosing. Endotracheal aspirates (ETA) or bronchiolar lavage (BAL) samples were plated out on agar plates to determine bacterial load. The results show that 11/39 patients with respiratory tract colonization with *Pseudomonas vaeruginosa* developed *Staphylococcus aureus* colonization. In 5/11 patients treated with the antibody the *Staphylococcus aureus* titer exceeded the *Pseudomonas aeruginosa* titer and in 4/5 of these patients there was a reduction (1/4) or complete elimination (3/4) of *Staphylococcus aureus* from the ETA and/or BAL fluid. These results are consistent with anti-PcrV antibody exerting an anti-Staphyloccal effect in patients colonized with high titers of *Staphyloccus aureus* and lower titers of *Pseudomonas aeruginosa*.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

All publications, accession numbers, patents, and patent applications cited in this specification are herein incorporated by reference as if each was specifically and individually indicated to be incorporated by reference.

Exemplary Anti-PcrV V-Regions of PcrV Antibodies for Use in the Invention

```
Exemplary Anti-PcrV V-regions of PcrV
antibodies for use in the invention
Vh (VH1)
                                          SEQ ID NO: 1
EIQLVQSGAEVKKPGASVKVSCKASGYTFTDHAISWVRQAPGQGLEWMG

WISPYSGNPNYAQSLQGRVSLTTDRSTRTAYMELRSLKSDDTAVYYCAR

NRGDIYYDFTYAFDIWGQGTMVTVSS

VkI
                                          SEQ ID NO: 2
DIQMTQSPSSVSASVGDRVTITCRASQGISSWLAWYQQKPGRAPKLLIY

AASSLQSGVPSRFSGSGSGTGFTLTISSLQPEDVATYYCQQFWSTPYTF

GQGTKLEIK

Vh
                                          SEQ ID NO: 3
QVQLVESGGGVVQPGGSLRLSCAASGFTFSTAGMHWVRQAPGKGLEWVA

VIWYNGKEISYADSVKGRFTVSRDNPKNTLYLQMSSLRTEDTAVYYCAR

NRGDIYYDFTYAMDIWGQGTMVTVSS

VkI
                                          SEQ ID NO: 4
DIQMTQSPSSLSASVGDRVTITCRASQSISRWVAWYQQRPGKAPNLLIY

DASSLKSGVPSRFSGSGSGTEFTLTISSLQPEDIATYYCQQFWSTPYTF

GQGTKLEIK

Vh
                                          SEQ ID NO: 5
QVQLVESGGGVVQPGRSLRLSCTASGFSFSSYGMHWVRQAPGKGLEWVA

VIWYNGKEISYADSVKGRFTVSRDNPKNTLYLQMSSLRTEDTAVYYCAR

NRGDIYYDFTYAMDIWGQGTMVTVSS

VkI
                                          SEQ ID NO: 6
AIQLTQSPSFLSASVGDRVTITCRASQGISTYLAWYQQKPGKAPKLLIY

AASSLQSGVPSRFSGSGSGTDFTLTISSLQPEDVATYYCQQFWSTPYTF

GQGTKLEIK

Vh
                                          SEQ ID NO: 7
QVQLVESGGGLVQPGRSLRLSCVGSGFTFSSYGIHWVRQAPGKGLEWVA

VIWYNGKEISYADSVKGRFTVSRDNLKNTLYLQMSSLRTEDTAVYYCAR

NRGDIYYDFTYAMDIWGQGTMVTVSS

VkI
                                          SEQ ID NO: 8
DIQMTQSPSFLSASVGDRVTITCRASQGISTYLAWYQQKRGKAPKLLIS

AASSLQSGVPSRFSGSVSGTDFTLTISSLQSEDFAVYYCQQFWSTPYTF

GQGTKLEIK

Vh
                                          SEQ ID NO: 9
QVQLVESGGGLVQPGRSLRLSCVGSGFTFSSYGIHWVRQAPGKGLEWVA

VIWYNGKEISYADSVKGRFTVSRDNPKNTLYLQMSSLRTEDTAVYYCAR

NRGDIYYDFTYAMDIWGQGTMVTVSS

VkI
                                          SEQ ID NO: 10
DIQLTQSPSFLSASVGDRVTITCRASQGISTYLAWYQQKPGKAPKLLIY

DASALQSGVPSRFSGSGSGTEFTLTISSLQPEDVATYYCQQFWSTPYTF

GQGTKLEIK

Vh
                                          SEQ ID NO: 11
EVQLVESGGGVVQPGGSLRLSCAASGFTFSTAGMHWVRQAPGKGLEWVA

VIWYNGKEISYADSVKGRFTVFRDNPKNTLYLQMSSLRTEDTAVYYCAR

NRGDIYYDFTYAMDIWGQGTMVTVSS

VkI
                                          SEQ ID NO: 12
DIQMTQSPSSLSASVGDRVTITCRASQSISRWVAWYQQRPGKAPNLLIY

DASSLKSGVPSRFSGSGSGTEFTLTISSLQPEDIATYYCQQFWSTPYTF

GQGTKLEIK

Vh
                                          SEQ ID NO: 13
QVQLVESGGGVVQPGRSLRLSCAASGFTFSSYPLHWVRQAPGKGLEWVS

FISYDGSEKYYASSVKGRFTISRDNSENTLYLQMNSLRPEDTAVYYCAR

NRGDIYYDFTYAMDIWGQGTMVTVSS

Vk
                                          SEQ ID NO: 14
DIQLTQSPSFLSASVGDRVTITCRASQGISTYLAWYQQKPGKAPKLLIY

DASALQSGVPSRFSGSGSGTEFTLTISSLQPEDVATYYCQQFWSTPYTF

GQGTKLEIK

Vh
                                          SEQ ID NO: 15
EVQLVESGGGVVQPGRSLRLSCTASGFSFSSYGMHWVRQAPGKGLEWVA

VIWYDGRNKYYADSVKGRFTISRDNSKNTLYLQMNSLRAEDTAVYYCAR

NRGDIYYDFTYAMDIWGQGTMVTVSS

VkIII
                                          SEQ ID NO: 16
EIVLTQFPGTLSLSPGERATLSCRASQNVGSAYLAWYQQKPGQAPRLLI

YGASRRAPGIPDRFSGSGSGTDFTLTINRLEPEDFAVYYCQQFWSTPYT

FGQGTKLEIK

Vh
                                          SEQ ID NO: 17
EVQLVESGGGVVQPGRSLRLSCAASGFTFSSYGMHWVRQAPGKGLEWVA

VIWYDGYNKDYADSVKGRFTISRDNSKNTLYLQINSLRAEDTAVYYCAR

NRGDIYYDFTYAMDIWGQGTMVTVSS

VkIII
                                          SEQ ID NO: 18
EIVMTQSPATLSVSPGERATLSCRASQSVSSNLAWYQQKPGQAPRLLIY

GASTRATGIPARFSGSGSGTEFTLTISSLQSEDFAVYYCQQFWSTPYTF

GQGTKLEIK
```

-continued

Vh
SEQ ID NO: 19
EVQLVESGGGVVQPGRSLRLSCAASGFTFSSYPLHWVRQAPGKGLEWVS
FISYDGSEKYYASSVKGRFTISRDNSENTLYLQMNSLRPEDTAVYYCAR
NRGDIYYDFTYAMDIWGQGTMVTVSS

VkIII
SEQ ID NO: 20
EIVMTQSPATLSVSPGERATLSCRASQSVSSNLAWYQQKPGQAPRLLFY
AASTRATGIPARFSGSGSGTEFTLTISSLQSEDFAVYYCQQFWSTPYTF
GQGTKLEIK

Vh
SEQ ID NO: 21
EVQLVESGGGLVQPGRSLRLSCVGSGFTFSSYGIHWVRQAPGKGLEWVA
NIWYDGSSESYIDSVKGRFTVSRDDSRNTVYLQMNSLRPEDTAVYYCAR
NRGDIYYDFTYAMDIWGQGTMVTVSS

VkIII
SEQ ID NO:22
EIVMTQSPATLSVSPGERATLSCRASQSVSSNLAWYQQKPGQAPRLLIY
GASTRATGIPARFSGSGSGTEFTLTISSLQSEDFAVYYCQQFWSTPYTF
GQGTKLEIK

VH
SEQ ID NO: 23
EVQLVESGGGVVQPGRSLRLSCAASGFTFSNYPMHWVRQAPGKGLEWVA
VISYDGSEKWYADSVKGRFTISRDNSKNTLYLEMNSLRPEDTAVYYCAR
NRGDIYYDFTYAMDQWGQGTTVTVSS

VK
SEQ ID NO: 24
DIQLTQSPSTLSASVGDSVTITCRASEGVDRWLAWYQQKPGRAPKLLIY
DASTLQSGVPSRFSGSGSGTEFSLTISSLQPDDVATYYCQHFWGTPYTF
GQGTKLEIK

VH
SEQ ID NO: 25
EVQLVESGGGVVQPGRSLRLSCAASGFTFSNYPMHWVRQAPGKGLEWVA
VISYDGSEKWYADSVKGRFTISRDNSKNTLYLEMNSLRPEDTAVYYCAR
NRGDIYYDFTYAMDSWGQGTTVTVSS

VK
SEQ ID NO: 24
DIQLTQSPSTLSASVGDSVTITCRASEGVDRWLAWYQQKPGRAPKLLIY
DASTLQSGVPSRFSGSGSGTEFSLTISSLQPDDVATYYCQHFWGTPYTF
GQGTKLEIK

VH
SEQ ID NO: 26
EVQLVESGGGVVQPGRSLRLSCAASGFTFSNYPMHWVRQAPGKGLEWVA
VISYDGSEKWYADSVKGRFTISRDNSKNTLYLEMNSLRPEDTAVYYCAR
NRGDIYYDFTYAMDIWGQGTTVTVSS

VK
SEQ ID NO: 24
DIQLTQSPSTLSASVGDSVTITCRASEGVDRWLAWYQQKPGRAPKLLIY
DASTLQSGVPSRFSGSGSGTEFSLTISSLQPDDVATYYCQHFWGTPYTF
GQGTKLEIK

-continued

VH
SEQ ID NO: 35
EVQLVESGGGVVQPGRSLRLSCAASGFTFSNYPMHWVRQAPGKGLEWVA
VISYDGSEKWYADSVKGRFTISRDNSKNTLYLEMNSLRPEDTAVYYCAR
NRGDIYYDFTYAMDYWGQGTTVTVSS

VK
SEQ ID NO: 36
DIQLTQSPSTLSASVGDSVTITCRASEGVDRWLAWYQQKPGRAPKLLIY
DASTLQSGVPSRFSGSGSGTEFSLTISSLQPDDVATYYCQHFWSTPYTF
GQGTKLEIK

V-regions of Exemplary Antibodies with
Lambda light chain

Vh
SEQ ID NO: 27
EVQLVESGGGVVQPGRSLRLSCAASGFTFSSYPLHWVRQAPGKGLEWVS
FISYDGSEKYYASSVKGRFTISRDNSENTLYLQMNSLRPEDTAVYYCAR
NRGDIYYDFTYAMDIWGQGTMVTVSS

Vl
SEQ ID no: 28
QSALTQPASVSGSPGQSITISCTGTSSDYVSWYQQHPGKAPKLIIYDVT
NRPSGVPDRFSGSKSGNTASLTISGLQAEDEADYYCQHFWSTPYTFGGG
TKLTVL

Vh
SEQ ID NO: 29
EVQLVESGGGVVQPGRSLRLSCAASGFTFSSYPLHWVRQAPGKGLEWVS
FISYDGSEKYYASSVKGRFTISRDNSENTLYLQMNSLRPEDTAVYYCAR
NRGDIYYDFTYAMDIWGQGTMVTVSS

Vl
SEQ ID NO: 30
SSELTQDPAVSVALGQTVRITCQGDSLRSYYASWYQQKPGQAPVLVIYG
KNNRPSGIPDRFSGSSSGNTASLTITGAQAEDEADYYCQHFWSTPYTFG
GGTKLTVL

Additional $V_L$ regions:
Vl
SEQ ID NO: 32
SSELTQDPAVSVALGQTVTITCQGDSLASLYASWYQQKPGQAPVLVLYS
KNSRPSGIPDRFSGSSSGNTASLTITGARAEDEADYYCQHFWSTPYTFG
GGTKLTVL Vl
SEQ ID NO: 34
QSVLTQPPSASGSPGQSVTISCTGTSSDVGAYNYVSWYQQYPGKVPKLI
IYEVTKRPSGVPDRFSGSKSGNTASLTVSGLRAEDEADYYCQHFWSTPY
TFGGGTKLTVL VkI
SEQ ID NO: 37
DIQMTQSPSSLSASVGDRVTITCRASQSISRWVAWYQQRPGKAPNLLIY
DASSLKSGVPSRFSGSGSGTEFTLTISSLQPEDIATYYCQQFWGTPYTF
GQGTKLEIK

What is claimed is:

1. A method of treating a *Staphylococcus aureus* infection in a patient who has a low level of *Pseudomonas aeruginosa* infection, the method comprising administering an anti-PcrV antibody that comprises a $V_H$ region and a $V_L$ region and is an antagonist of the *Pseudomonas aeruginosa* Type III secretion system (TTSS), to the patient in an amount to effectively reduce the *Staphylococcus aureus* load in the patient.

2. The method of claim 1, wherein the patient has cystic fibrosis, is on a mechanical ventilator, is a neutropenic cancer patient, or is a burn patient.

3. The method of claim 1, wherein the level of TTSS-expressing *Pseudomonas aeruginosa* is 10% or greater of the *Pseudomonas aeruginosa* burden.

4. The method of claim 1, further comprising administering a penicillinase-resistant penicillin.

5. The method of claim 1, further comprising administering a Gram-positive selective antibiotic.

6. The method of claim 5, wherein the Gram-positive-selective antibiotic is vancomycin or daptomycin.

7. The method of claim 1, wherein the patient has cystic fibrosis and the method further comprises administering an antibiotic with the proviso that the antibiotic is not an aminoglycoside.

8. The method of claim 1, wherein the anti-PcrV antibody competes with Mab166 for binding to PcrV.

9. The method of claim 8, wherein the antibody has a $V_H$ region that has a CDR1 that comprises NYPMH (SEQ ID NO:56), a CDR2 that comprises VISYDGSEKWYADSVKG (SEQ ID NO:57), and a CDR3 that comprises NRGDIYYD-FTYAMDI (SEQ ID NO:50); and a $V_L$ region that has a CDR1 that comprises RASEGVDRWLA (SEQ ID NO:58), a CDR2 that comprises DASTLQS (SEQ ID NO:59), and a CDR3 that comprises QHFWGTPYT (SEQ ID NO:48).

10. The method of claim 1, wherein the $V_H$ region has the amino acid sequence of SEQ ID NO:1, 3, 5, 7, 9, 11, 13, 15, 17, 19, 21, 23, 25, 26, or 35.

11. The method of claim 1, wherein the $V_L$ region has the amino acid sequence of SEQ ID NO:2, 4, 6, 8, 10, 12, 14, 16, 18, 20, 22, 24, 28, 30, 32, 34, 36, 37, 43, or 44.

12. The method of claim 1, wherein the antibody is a Fab'.

13. The method of claim 1, wherein the antibody is PEGylated.

14. A method of treating a mechanically ventilated patient infected with *Staphylococcus aureus* and *Pseudomonas aeruginosa*, where the levels of *Staphylococcus aureus* and *Pseudomonas aeruginosa* are each $10^3$ cfu/ml, or less, in an endotracheal aspirate; or $10^2$ cfu/ml, or less, in a bronchoalveolar lavage, the method comprising administering a therapeutically effective dose of an anti-PcrV antibody to the patient, wherein the anti-PcrV antibody comprises a VH region and a VL region and is an antagonist of the Type III secretion system.

15. The method of claim 14, wherein the anti-PcrV antibody competes with Mab166 for binding to PcrV.

16. The method of claim 15, wherein the antibody has a $V_H$ region that has a CDR1 that comprises NYPMH (SEQ ID NO:56), a CDR2 that comprises VISYDGSEKWYADSVKG (SEQ ID NO:57), and a CDR3 that comprises NRGDIYYD-FTYAMDI (SEQ ID NO:50); and a $V_L$ region that has a CDR1 that comprises RASEGVDRWLA (SEQ ID NO:58), a CDR2 that comprises DASTLQS (SEQ ID NO:59), and a CDR3 that comprises QHFWGTPYT (SEQ ID NO:48).

17. The method of claim 14, wherein the $V_H$ region has the amino acid sequence of SEQ ID NO:1, 3, 5, 7, 9, 11, 13, 15, 17, 19, 21, 23, 25, 26, or 35.

18. The method of claim 14, wherein the antibody comprises a $V_L$ region that has the amino acid sequence of SEQ NO:2, 4, 6, 8, 10, 12, 14, 16, 18, 20, 22, 24, 28, 30, 32, 36, 37, 43, or 44.

19. A method of treating a patient with a wound infected with *Staphylococcus aureus* and *Pseudomonas aeruginosa*, where the levels of *Staphylococcus aureus* and *Pseudomonas aeruginosa* are each less than $10^3$ cfu/g of tissue or less than $10^3$ cfu/ml of exudate, the method comprising administering a therapeutically effective dose of an anti-PcrV antibody to the patient, wherein the anti-PcrV antibody comprises a VH region and a VL region and is an antagonist of the Type III secretion system.

20. The method of claim 19, wherein the anti-PcrV antibody competes with Mab166 for binding to PcrV.

21. The method of claim 20, wherein the antibody has a $V_H$ region that has a CDR1 that comprises NYPMH (SEQ ID NO:56), a CDR2 that comprises VISYDGSEKWYADSVKG (SEQ ID NO:57), and a CDR3 that comprises NRGDIYYD-FTYAMDI (SEQ ID NO:50); and a $V_L$ region that has a CDR1 that comprises RASEGVDRWLA (SEQ ID NO:58), a CDR2 that comprises DASTLQS (SEQ ID NO:59), and a CDR3 that comprises QHFWGTPYT (SEQ ID NO:48).

22. The method of claim 19, wherein the $V_H$ region has the amino acid sequence of SEQ ID NO:1, 3, 5, 7, 9, 11, 13, 15, 17, 19, 21, 23, 25, 26, or 35.

23. The method of claim 19, wherein the $V_L$ region has the amino acid sequence of SEQ ID NO:2, 4, 6, 8, 10, 12, 14, 16, 18, 20, 22, 24, 28, 30, 32, 36, 37, 43, or 44.

24. The method of claim 1, wherein the antibody comprises a $V_H$ region having the amino acid sequence of SEQ ID NO:26 and a $V_L$ region having the amino acid sequence of SEQ ID NO:24.

25. The method of claim 14, wherein the antibody comprises a $V_H$ region having the amino acid sequence of SEQ ID NO:26 and a $V_L$ region having the amino acid sequence of SEQ ID NO:24.

26. The method of claim 19, wherein the antibody comprises a $V_H$ region having the amino acid sequence of SEQ ID NO:26 and a $V_L$ region having the amino acid sequence of SEQ ID NO:24.

* * * * *

SEQUENCE LISTING

<160> NUMBER OF SEQ ID NOS: 59

<210> SEQ ID NO 1
<211> LENGTH: 124
<212> TYPE: PRT
<213> ORGANISM: Homo sapiens
<220> FEATURE:
<223> OTHER INFORMATION: anti-type III secretion system (TTSS) V antigen
      (anti-PcrV) antibody VH1 Vh region

<400> SEQUENCE: 1

Glu Ile Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp His
            20                  25                  30

Ala Ile Ser Trp Val Arg Gln Ala Pro Gly Gln Gly Leu Glu Trp Met
        35                  40                  45

Gly Trp Ile Ser Pro Tyr Ser Gly Asn Pro Asn Tyr Ala Gln Ser Leu
    50                  55                  60

Gln Gly Arg Val Ser Leu Thr Thr Asp Arg Ser Thr Arg Thr Ala Tyr
65                  70                  75                  80

Met Glu Leu Arg Ser Leu Lys Ser Asp Asp Thr Ala Val Tyr Tyr Cys
                85                  90                  95

Ala Arg Asn Arg Gly Asp Ile Tyr Tyr Asp Phe Thr Tyr Ala Phe Asp
            100                 105                 110

Ile Trp Gly Gln Gly Thr Met Val Thr Val Ser Ser
        115                 120

<210> SEQ ID NO 2
<211> LENGTH: 107
<212> TYPE: PRT
<213> ORGANISM: Homo sapiens
<220> FEATURE:
<223> OTHER INFORMATION: anti-type III secretion system (TTSS) V antigen
      (anti-PcrV) antibody VkappaI subclass V-L region

<400> SEQUENCE: 2

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Ser Trp
            20                  25                  30

Leu Ala Trp Tyr Gln Gly Lys Pro Gly Arg Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Val Ala Thr Tyr Tyr Cys Gln Gln Phe Trp Ser Thr Pro Tyr
                85                  90                  95

Thr Phe Gly Gln Gly Thr Lys Leu Glu Ile Lys
            100                 105

<210> SEQ ID NO 3
<211> LENGTH: 124
<212> TYPE: PRT
<213> ORGANISM: Homo sapiens
<220> FEATURE:
<223> OTHER INFORMATION: anti-type III secretion system (TTSS) V antigen
      (anti-PcrV) antibody VH3 Vh region

```
<400> SEQUENCE: 3

Gln Val Gln Leu Val Glu Ser Gly Gly Val Val Gln Pro Gly Gly
  1               5                  10                  15

Ser Leu Arg Leu Ser Cys Ala Ala Ser Gly Phe Thr Phe Ser Thr Ala
             20                  25                  30

Gly Met His Trp Val Arg Gln Ala Pro Gly Lys Gly Leu Glu Trp Val
         35                  40                  45

Ala Val Ile Trp Tyr Asn Gly Lys Glu Ile Ser Tyr Ala Asp Ser Val
 50                  55                  60

Lys Gly Arg Phe Thr Val Ser Arg Asp Asn Pro Lys Asn Thr Leu Tyr
 65                  70                  75                  80

Leu Gln Met Ser Ser Leu Arg Thr Glu Asp Thr Ala Val Tyr Tyr Cys
                 85                  90                  95

Ala Arg Asn Arg Gly Asp Ile Tyr Tyr Asp Phe Thr Tyr Ala Met Asp
             100                 105                 110

Ile Trp Gly Gln Gly Thr Met Val Thr Val Ser Ser
             115                 120

<210> SEQ ID NO 4
<211> LENGTH: 107
<212> TYPE: PRT
<213> ORGANISM: Homo sapiens
<220> FEATURE:
<223> OTHER INFORMATION: anti-type III secretion system (TTSS) V antigen
      (anti-PcrV) antibody VkappaI subclass V-L region

<400> SEQUENCE: 4

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Arg Trp
             20                  25                  30

Val Ala Trp Tyr Gln Gln Arg Pro Gly Lys Ala Pro Asn Leu Leu Ile
         35                  40                  45

Tyr Asp Ala Ser Ser Leu Lys Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Ile Ala Thr Tyr Tyr Cys Gln Gln Phe Trp Ser Thr Pro Tyr
                 85                  90                  95

Thr Phe Gly Gln Gly Thr Lys Leu Glu Ile Lys
             100                 105

<210> SEQ ID NO 5
<211> LENGTH: 124
<212> TYPE: PRT
<213> ORGANISM: Homo sapiens
<220> FEATURE:
<223> OTHER INFORMATION: anti-type III secretion system (TTSS) V antigen
      (anti-PcrV) antibody VH3 Vh region

<400> SEQUENCE: 5

Gln Val Gln Leu Val Glu Ser Gly Gly Val Val Gln Pro Gly Arg
  1               5                  10                  15

Ser Leu Arg Leu Ser Cys Thr Ala Ser Gly Phe Ser Phe Ser Ser Tyr
             20                  25                  30

Gly Met His Trp Val Arg Gln Ala Pro Gly Lys Gly Leu Glu Trp Val
         35                  40                  45

Ala Val Ile Trp Tyr Asn Gly Lys Glu Ile Ser Tyr Ala Asp Ser Val
 50                  55                  60
```

```
Lys Gly Arg Phe Thr Val Ser Arg Asp Asn Pro Lys Asn Thr Leu Tyr
 65                  70                  75                  80

Leu Gln Met Ser Ser Leu Arg Thr Glu Asp Thr Ala Val Tyr Tyr Cys
                 85                  90                  95

Ala Arg Asn Arg Gly Asp Ile Tyr Tyr Asp Phe Thr Tyr Ala Met Asp
            100                 105                 110

Ile Trp Gly Gln Gly Thr Met Val Thr Val Ser Ser
        115                 120

<210> SEQ ID NO 6
<211> LENGTH: 107
<212> TYPE: PRT
<213> ORGANISM: Homo sapiens
<220> FEATURE:
<223> OTHER INFORMATION: anti-type III secretion system (TTSS) V antigen
      (anti-PcrV) antibody VkappaI subclass V-L region

<400> SEQUENCE: 6

Ala Ile Gln Leu Thr Gln Ser Pro Ser Phe Leu Ser Ala Ser Val Gly
 1               5                  10                  15

Asp Arg Val Thr Ile Thr Cys Arg Ala Ser Gln Gly Ile Ser Thr Tyr
             20                  25                  30

Leu Ala Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Gln Phe Trp Ser Thr Pro Tyr
                 85                  90                  95

Thr Phe Gly Gln Gly Thr Lys Leu Glu Ile Lys
            100                 105

<210> SEQ ID NO 7
<211> LENGTH: 124
<212> TYPE: PRT
<213> ORGANISM: Homo sapiens
<220> FEATURE:
<223> OTHER INFORMATION: anti-type III secretion system (TTSS) V antigen
      (anti-PcrV) antibody VH3 Vh region

<400> SEQUENCE: 7

Gln Val Gln Leu Val Glu Ser Gly Gly Gly Leu Val Gln Pro Gly Arg
 1               5                  10                  15

Ser Leu Arg Leu Ser Cys Val Gly Ser Gly Phe Thr Phe Ser Ser Tyr
             20                  25                  30

Gly Ile His Trp Val Arg Gln Ala Pro Gly Lys Gly Leu Glu Trp Val
         35                  40                  45

Ala Val Ile Trp Tyr Asn Gly Lys Glu Ile Ser Tyr Ala Asp Ser Val
     50                  55                  60

Lys Gly Arg Phe Thr Val Ser Arg Asp Asn Leu Lys Asn Thr Leu Tyr
 65                  70                  75                  80

Leu Gln Met Ser Ser Leu Arg Thr Glu Asp Thr Ala Val Tyr Tyr Cys
                 85                  90                  95

Ala Arg Asn Arg Gly Asp Ile Tyr Tyr Asp Phe Thr Tyr Ala Met Asp
            100                 105                 110

Ile Trp Gly Gln Gly Thr Met Val Thr Val Ser Ser
        115                 120
```

```
<210> SEQ ID NO 8
<211> LENGTH: 107
<212> TYPE: PRT
<213> ORGANISM: Homo sapiens
<220> FEATURE:
<223> OTHER INFORMATION: anti-type III secretion system (TTSS) V antigen
      (anti-PcrV) antibody VkappaI subclass V-L region

<400> SEQUENCE: 8

Asp Ile Gln Met Thr Gln Ser Pro Ser Phe Leu Ser Ala Ser Val Gly
 1               5                  10                  15

Asp Arg Val Thr Ile Thr Cys Arg Ala Ser Gln Gly Ile Ser Thr Tyr
                20                  25                  30

Leu Ala Trp Tyr Gln Gln Lys Arg Gly Lys Ala Pro Lys Leu Leu Ile
            35                  40                  45

Ser Ala Ala Ser Ser Leu Gln Ser Gly Val Pro Ser Arg Phe Ser Gly
50                  55                  60

Ser Val Ser Gly Thr Asp Phe Thr Leu Thr Ile Ser Ser Leu Gln Ser
65                  70                  75                  80

Glu Asp Phe Ala Val Tyr Tyr Cys Gln Gln Phe Trp Ser Thr Pro Tyr
                85                  90                  95

Thr Phe Gly Gln Gly Thr Lys Leu Glu Ile Lys
            100                 105

<210> SEQ ID NO 9
<211> LENGTH: 124
<212> TYPE: PRT
<213> ORGANISM: Homo sapiens
<220> FEATURE:
<223> OTHER INFORMATION: anti-type III secretion system (TTSS) V antigen
      (anti-PcrV) antibody VH3 Vh region

<400> SEQUENCE: 9

Gln Val Gln Leu Val Glu Ser Gly Gly Gly Leu Val Gln Pro Gly Arg
 1               5                  10                  15

Ser Leu Arg Leu Ser Cys Val Gly Ser Gly Phe Thr Phe Ser Ser Tyr
                20                  25                  30

Gly Ile His Trp Val Arg Gln Ala Pro Gly Lys Gly Leu Glu Trp Val
            35                  40                  45

Ala Val Ile Trp Tyr Asn Gly Lys Glu Ile Ser Tyr Ala Asp Ser Val
50                  55                  60

Lys Gly Arg Phe Thr Val Ser Arg Asp Asn Pro Lys Asn Thr Leu Tyr
65                  70                  75                  80

Leu Gln Met Ser Ser Leu Arg Thr Glu Asp Thr Ala Val Tyr Tyr Cys
                85                  90                  95

Ala Arg Asn Arg Gly Asp Ile Tyr Tyr Asp Phe Thr Tyr Ala Met Asp
            100                 105                 110

Ile Trp Gly Gln Gly Thr Met Val Thr Val Ser Ser
            115                 120

<210> SEQ ID NO 10
<211> LENGTH: 107
<212> TYPE: PRT
<213> ORGANISM: Homo sapiens
<220> FEATURE:
<223> OTHER INFORMATION: anti-type III secretion system (TTSS) V antigen
      (anti-PcrV) antibody VkappaI subclass V-L region
```

-continued

```
<400> SEQUENCE: 10

Asp Ile Gln Leu Thr Gln Ser Pro Ser Phe Leu Ser Ala Ser Val Gly
 1               5                  10                  15

Asp Arg Val Thr Ile Thr Cys Arg Ala Ser Gln Gly Ile Ser Thr Tyr
             20                  25                  30

Leu Ala Trp Tyr Gln Gln Lys Pro Gly Lys Ala Pro Lys Leu Leu Ile
         35                  40                  45

Tyr Asp Ala Ser Ala Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Val Ala Thr Tyr Tyr Cys Gln Gln Phe Trp Ser Thr Pro Tyr
                 85                  90                  95

Thr Phe Gly Gln Gly Thr Lys Leu Glu Ile Lys
            100                 105

<210> SEQ ID NO 11
<211> LENGTH: 124
<212> TYPE: PRT
<213> ORGANISM: Homo sapiens
<220> FEATURE:
<223> OTHER INFORMATION: anti-type III secretion system (TTSS) V antigen
      (anti-PcrV) antibody VH3 Vh region

<400> SEQUENCE: 11

Glu Val Gln Leu Val Glu Ser Gly Gly Val Val Gln Pro Gly Gly
 1               5                  10                  15

Ser Leu Arg Leu Ser Cys Ala Ala Ser Gly Phe Thr Phe Ser Thr Ala
             20                  25                  30

Gly Met His Trp Val Arg Gln Ala Pro Gly Lys Gly Leu Glu Trp Val
         35                  40                  45

Ala Val Ile Trp Tyr Asn Gly Lys Glu Ile Ser Tyr Ala Asp Ser Val
 50                  55                  60

Lys Gly Arg Phe Thr Val Phe Arg Asp Asn Pro Lys Asn Thr Leu Tyr
 65                  70                  75                  80

Leu Gln Met Ser Ser Leu Arg Thr Glu Asp Thr Ala Val Tyr Tyr Cys
                 85                  90                  95

Ala Arg Asn Arg Gly Asp Ile Tyr Tyr Asp Phe Thr Tyr Ala Met Asp
            100                 105                 110

Ile Trp Gly Gln Gly Thr Met Val Thr Val Ser Ser
        115                 120

<210> SEQ ID NO 12
<211> LENGTH: 107
<212> TYPE: PRT
<213> ORGANISM: Homo sapiens
<220> FEATURE:
<223> OTHER INFORMATION: anti-type III secretion system (TTSS) V antigen
      (anti-PcrV) antibody VkappaI subclass V-L region

<400> SEQUENCE: 12

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Arg Trp
             20                  25                  30

Val Ala Trp Tyr Gln Gln Arg Pro Gly Lys Ala Pro Asn Leu Leu Ile
         35                  40                  45

Tyr Asp Ala Ser Ser Leu Lys Ser Gly Val Pro Ser Arg Phe Ser Gly
 50                  55                  60
```

Ser Gly Ser Gly Thr Glu Phe Thr Leu Thr Ile Ser Ser Leu Gln Pro
65                  70                  75                  80

Glu Asp Ile Ala Thr Tyr Tyr Cys Gln Gln Phe Trp Ser Thr Pro Tyr
                85                  90                  95

Thr Phe Gly Gln Gly Thr Lys Leu Glu Ile Lys
            100                 105

<210> SEQ ID NO 13
<211> LENGTH: 124
<212> TYPE: PRT
<213> ORGANISM: Homo sapiens
<220> FEATURE:
<223> OTHER INFORMATION: anti-type III secretion system (TTSS) V antigen
      (anti-PcrV) antibody VH3 Vh region

<400> SEQUENCE: 13

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Pro Leu His Trp Val Arg Gln Ala Pro Gly Lys Gly Leu Glu Trp Val
            35                  40                  45

Ser Phe Ile Ser Tyr Asp Gly Ser Glu Lys Tyr Tyr Ala Ser Ser Val
        50                  55                  60

Lys Gly Arg Phe Thr Ile Ser Arg Asp Asn Ser Glu Asn Thr Leu Tyr
65                  70                  75                  80

Leu Gln Met Asn Ser Leu Arg Pro Glu Asp Thr Ala Val Tyr Tyr Cys
                85                  90                  95

Ala Arg Asn Arg Gly Asp Ile Tyr Tyr Asp Phe Thr Tyr Ala Met Asp
            100                 105                 110

Ile Trp Gly Gln Gly Thr Met Val Thr Val Ser Ser
        115                 120

<210> SEQ ID NO 14
<211> LENGTH: 107
<212> TYPE: PRT
<213> ORGANISM: Homo sapiens
<220> FEATURE:
<223> OTHER INFORMATION: anti-type III secretion system (TTSS) V antigen
      (anti-PcrV) antibody VkappaI subclass V-L region

<400> SEQUENCE: 14

Asp Ile Gln Leu Thr Gln Ser Pro Ser Phe Leu Ser Ala Ser Val Gly
 1               5                  10                  15

Asp Arg Val Thr Ile Thr Cys Arg Ala Ser Gln Gly Ile Ser Thr Tyr
                20                  25                  30

Leu Ala Trp Tyr Gln Gln Lys Pro Gly Lys Ala Pro Lys Leu Leu Ile
            35                  40                  45

Tyr Asp Ala Ser Ala Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Val Ala Thr Tyr Tyr Cys Gln Gln Phe Trp Ser Thr Pro Tyr
                85                  90                  95

Thr Phe Gly Gln Gly Thr Lys Leu Glu Ile Lys
            100                 105

```
<210> SEQ ID NO 15
<211> LENGTH: 124
<212> TYPE: PRT
<213> ORGANISM: Homo sapiens
<220> FEATURE:
<223> OTHER INFORMATION: anti-type III secretion system (TTSS) V antigen
      (anti-PcrV) antibody VH3 Vh region

<400> SEQUENCE: 15
```

Glu Val Gln Leu Val Glu Ser Gly Gly Gly Val Val Gln Pro Gly Arg
1               5                   10                  15

Ser Leu Arg Leu Ser Cys Thr Ala Ser Gly Phe Ser Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Arg Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Arg Gly Asp Ile Tyr Tyr Asp Phe Thr Tyr Ala Met Asp
            100                 105                 110

Ile Trp Gly Gln Gly Thr Met Val Thr Val Ser Ser
        115                 120

```
<210> SEQ ID NO 16
<211> LENGTH: 108
<212> TYPE: PRT
<213> ORGANISM: Homo sapiens
<220> FEATURE:
<223> OTHER INFORMATION: anti-type III secretion system (TTSS) V antigen
      (anti-PcrV) antibody VkappaIII subclass V-L region

<400> SEQUENCE: 16
```

Glu Ile Val Leu Thr Gln Phe Pro Gly Thr Leu Ser Leu Ser Pro Gly
1               5                   10                  15

Glu Arg Ala Thr Leu Ser Cys Arg Ala Ser Gln Asn Val Gly Ser Ala
            20                  25                  30

Tyr Leu Ala Trp Tyr Gln Gln Lys Pro Gly Gln Ala Pro Arg Leu Leu
        35                  40                  45

Ile Tyr Gly Ala Ser Arg Arg Ala Pro Gly Ile Pro Asp Arg Phe Ser
    50                  55                  60

Gly Ser Gly Ser Gly Thr Asp Phe Thr Leu Thr Ile Asn Arg Leu Glu
65                  70                  75                  80

Pro Glu Asp Phe Ala Val Tyr Tyr Cys Gln Gln Phe Trp Ser Thr Pro
                85                  90                  95

Tyr Thr Phe Gly Gln Gly Thr Lys Leu Glu Ile Lys
            100                 105

```
<210> SEQ ID NO 17
<211> LENGTH: 124
<212> TYPE: PRT
<213> ORGANISM: Homo sapiens
<220> FEATURE:
<223> OTHER INFORMATION: anti-type III secretion system (TTSS) V antigen
      (anti-PcrV) antibody VH3 Vh region
```

<400> SEQUENCE: 17

Glu Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Tyr Asn Lys Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Ile Asn Ser Leu Arg Ala Glu Asp Thr Ala Val Tyr Tyr Cys
                85                  90                  95

Ala Arg Asn Arg Gly Asp Ile Tyr Tyr Asp Phe Thr Tyr Ala Met Asp
            100                 105                 110

Ile Trp Gly Gln Gly Thr Met Val Thr Val Ser Ser
        115                 120

<210> SEQ ID NO 18
<211> LENGTH: 107
<212> TYPE: PRT
<213> ORGANISM: Homo sapiens
<220> FEATURE:
<223> OTHER INFORMATION: anti-type III secretion system (TTSS) V antigen
      (anti-PcrV) antibody VkappaIII subclass V-L region

<400> SEQUENCE: 18

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Phe Trp Ser Thr Pro Tyr
                85                  90                  95

Thr Phe Gly Gln Gly Thr Lys Leu Glu Ile Lys
            100                 105

<210> SEQ ID NO 19
<211> LENGTH: 124
<212> TYPE: PRT
<213> ORGANISM: Homo sapiens
<220> FEATURE:
<223> OTHER INFORMATION: anti-type III secretion system (TTSS) V antigen
      (anti-PcrV) antibody VH3 Vh region

<400> SEQUENCE: 19

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Pro Leu His Trp Val Arg Gln Ala Pro Gly Lys Gly Leu Glu Trp Val
        35                  40                  45

Ser Phe Ile Ser Tyr Asp Gly Ser Glu Lys Tyr Tyr Ala Ser Ser Val
    50                  55                  60

```
Lys Gly Arg Phe Thr Ile Ser Arg Asp Asn Ser Glu Asn Thr Leu Tyr
 65                  70                  75                  80

Leu Gln Met Asn Ser Leu Arg Pro Glu Asp Thr Ala Val Tyr Tyr Cys
                 85                  90                  95

Ala Arg Asn Arg Gly Asp Ile Tyr Tyr Asp Phe Thr Tyr Ala Met Asp
            100                 105                 110

Ile Trp Gly Gln Gly Thr Met Val Thr Val Ser Ser
        115                 120

<210> SEQ ID NO 20
<211> LENGTH: 107
<212> TYPE: PRT
<213> ORGANISM: Homo sapiens
<220> FEATURE:
<223> OTHER INFORMATION: anti-type III secretion system (TTSS) V antigen
      (anti-PcrV) antibody VkappaIII subclass V-L region

<400> SEQUENCE: 20

Glu Ile Val Met Thr Gln Ser Pro Ala Thr Leu Ser Val Ser Pro Gly
  1               5                  10                  15

Glu Arg Ala Thr Leu Ser Cys Arg Ala Ser Gln Ser Val Ser Ser Asn
             20                  25                  30

Leu Ala Trp Tyr Gln Gln Lys Pro Gly Gln Ala Pro Arg Leu Leu Phe
         35                  40                  45

Tyr Ala Ala Ser Thr Arg Ala Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Trp Ser Thr Pro Tyr
                 85                  90                  95

Thr Phe Gly Gln Gly Thr Lys Leu Glu Ile Lys
            100                 105

<210> SEQ ID NO 21
<211> LENGTH: 124
<212> TYPE: PRT
<213> ORGANISM: Homo sapiens
<220> FEATURE:
<223> OTHER INFORMATION: anti-type III secretion system (TTSS) V antigen
      (anti-PcrV) antibody VH3 Vh region

<400> SEQUENCE: 21

Glu Val Gln Leu Val Glu Ser Gly Gly Gly Leu Val Gln Pro Gly Arg
  1               5                  10                  15

Ser Leu Arg Leu Ser Cys Val Gly Ser Gly Phe Thr Phe Ser Ser Tyr
             20                  25                  30

Gly Ile His Trp Val Arg Gln Ala Pro Gly Lys Gly Leu Glu Trp Val
         35                  40                  45

Ala Asn Ile Trp Tyr Asp Gly Ser Ser Glu Ser Tyr Ile Asp Ser Val
 50                  55                  60

Lys Gly Arg Phe Thr Val Ser Arg Asp Asp Ser Arg Asn Thr Val Tyr
 65                  70                  75                  80

Leu Gln Met Asn Ser Leu Arg Pro Glu Asp Thr Ala Val Tyr Tyr Cys
                 85                  90                  95

Ala Arg Asn Arg Gly Asp Ile Tyr Tyr Asp Phe Thr Tyr Ala Met Asp
            100                 105                 110

Ile Trp Gly Gln Gly Thr Met Val Thr Val Ser Ser
        115                 120
```

```
<210> SEQ ID NO 22
<211> LENGTH: 107
<212> TYPE: PRT
<213> ORGANISM: Homo sapiens
<220> FEATURE:
<223> OTHER INFORMATION: anti-type III secretion system (TTSS) V antigen
      (anti-PcrV) antibody VkappaIII subclass V-L region

<400> SEQUENCE: 22

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Phe Trp Ser Thr Pro Tyr
                85                  90                  95

Thr Phe Gly Gln Gly Thr Lys Leu Glu Ile Lys
            100                 105

<210> SEQ ID NO 23
<211> LENGTH: 124
<212> TYPE: PRT
<213> ORGANISM: Homo sapiens
<220> FEATURE:
<223> OTHER INFORMATION: anti-type III secretion system (TTSS) V antigen
      (anti-PcrV) antibody VH3 Vh region

<400> SEQUENCE: 23

Glu Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Asn Tyr
            20                  25                  30

Pro Met His Trp Val Arg Gln Ala Pro Gly Lys Gly Leu Glu Trp Val
        35                  40                  45

Ala Val Ile Ser Tyr Asp Gly Ser Glu Lys Trp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Glu Met Asn Ser Leu Arg Pro Glu Asp Thr Ala Val Tyr Tyr Cys
                85                  90                  95

Ala Arg Asn Arg Gly Asp Ile Tyr Tyr Asp Phe Thr Tyr Ala Met Asp
            100                 105                 110

Gln Trp Gly Gln Gly Thr Thr Val Thr Val Ser Ser
        115                 120

<210> SEQ ID NO 24
<211> LENGTH: 107
<212> TYPE: PRT
<213> ORGANISM: Homo sapiens
<220> FEATURE:
<223> OTHER INFORMATION: anti-type III secretion system (TTSS) V antigen
      (anti-PcrV) antibody VkappaI subclass V-L region
```

-continued

<400> SEQUENCE: 24

Asp Ile Gln Leu Thr Gln Ser Pro Ser Thr Leu Ser Ala Ser Val Gly
1               5                   10                  15

Asp Ser Val Thr Ile Thr Cys Arg Ala Ser Glu Gly Val Asp Arg Trp
            20                  25                  30

Leu Ala Trp Tyr Gln Gln Lys Pro Gly Arg Ala Pro Lys Leu Leu Ile
        35                  40                  45

Tyr Asp Ala Ser Thr Leu Gln Ser Gly Val Pro Ser Arg Phe Ser Gly
50                  55                  60

Ser Gly Ser Gly Thr Glu Phe Ser Leu Thr Ile Ser Ser Leu Gln Pro
65                  70                  75                  80

Asp Asp Val Ala Thr Tyr Tyr Cys Gln His Phe Trp Gly Thr Pro Tyr
                85                  90                  95

Thr Phe Gly Gln Gly Thr Lys Leu Glu Ile Lys
            100                 105

<210> SEQ ID NO 25
<211> LENGTH: 124
<212> TYPE: PRT
<213> ORGANISM: Homo sapiens
<220> FEATURE:
<223> OTHER INFORMATION: anti-type III secretion system (TTSS) V antigen
      (anti-PcrV) antibody VH3 Vh region

<400> SEQUENCE: 25

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Pro Met His Trp Val Arg Gln Ala Pro Gly Lys Gly Leu Glu Trp Val
        35                  40                  45

Ala Val Ile Ser Tyr Asp Gly Ser Glu Lys Trp Tyr Ala Asp Ser Val
50                  55                  60

Lys Gly Arg Phe Thr Ile Ser Arg Asp Asn Ser Lys Asn Thr Leu Tyr
65                  70                  75                  80

Leu Glu Met Asn Ser Leu Arg Pro Glu Asp Thr Ala Val Tyr Tyr Cys
                85                  90                  95

Ala Arg Asn Arg Gly Asp Ile Tyr Tyr Asp Phe Thr Tyr Ala Met Asp
            100                 105                 110

Ser Trp Gly Gln Gly Thr Thr Val Thr Val Ser Ser
        115                 120

<210> SEQ ID NO 26
<211> LENGTH: 124
<212> TYPE: PRT
<213> ORGANISM: Homo sapiens
<220> FEATURE:
<223> OTHER INFORMATION: anti-type III secretion system (TTSS) V antigen
      (anti-PcrV) antibody VH3 Vh region

<400> SEQUENCE: 26

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Pro Met His Trp Val Arg Gln Ala Pro Gly Lys Gly Leu Glu Trp Val
        35                  40                  45

Ala Val Ile Ser Tyr Asp Gly Ser Glu Lys Trp Tyr Ala Asp Ser Val
50                  55                  60

```
Lys Gly Arg Phe Thr Ile Ser Arg Asp Asn Ser Lys Asn Thr Leu Tyr
 65                  70                  75                  80

Leu Glu Met Asn Ser Leu Arg Pro Glu Asp Thr Ala Val Tyr Tyr Cys
                 85                  90                  95

Ala Arg Asn Arg Gly Asp Ile Tyr Tyr Asp Phe Thr Tyr Ala Met Asp
            100                 105                 110

Ile Trp Gly Gln Gly Thr Thr Val Thr Val Ser Ser
        115                 120

<210> SEQ ID NO 27
<211> LENGTH: 124
<212> TYPE: PRT
<213> ORGANISM: Homo sapiens
<220> FEATURE:
<223> OTHER INFORMATION: anti-type III secretion system (TTSS) V antigen
      (anti-PcrV) antibody VH3 Vh region

<400> SEQUENCE: 27

Glu Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                 20                  25                  30

Pro Leu His Trp Val Arg Gln Ala Pro Gly Lys Gly Leu Glu Trp Val
             35                  40                  45

Ser Phe Ile Ser Tyr Asp Gly Ser Glu Lys Tyr Tyr Ala Ser Ser Val
         50                  55                  60

Lys Gly Arg Phe Thr Ile Ser Arg Asp Asn Ser Glu Asn Thr Leu Tyr
 65                  70                  75                  80

Leu Gln Met Asn Ser Leu Arg Pro Glu Asp Thr Ala Val Tyr Tyr Cys
                 85                  90                  95

Ala Arg Asn Arg Gly Asp Ile Tyr Tyr Asp Phe Thr Tyr Ala Met Asp
            100                 105                 110

Ile Trp Gly Gln Gly Thr Met Val Thr Val Ser Ser
        115                 120

<210> SEQ ID NO 28
<211> LENGTH: 104
<212> TYPE: PRT
<213> ORGANISM: Homo sapiens
<220> FEATURE:
<223> OTHER INFORMATION: anti-type III secretion system (TTSS) V antigen
      (anti-PcrV) antibody Vlambda subclass V-L region

<400> SEQUENCE: 28

Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Tyr Val Ser Trp
                 20                  25                  30

Tyr Gln Gln His Pro Gly Lys Ala Pro Lys Leu Ile Ile Tyr Asp Val
             35                  40                  45

Thr Asn Arg Pro Ser Gly Val Pro Asp Arg Phe Ser Gly Ser Lys Ser
         50                  55                  60

Gly Asn Thr Ala Ser Leu Thr Ile Ser Gly Leu Gln Ala Glu Asp Glu
 65                  70                  75                  80

Ala Asp Tyr Tyr Cys Gln His Phe Trp Ser Thr Pro Tyr Thr Phe Gly
                 85                  90                  95

Gly Gly Thr Lys Leu Thr Val Leu
            100
```

```
<210> SEQ ID NO 29
<211> LENGTH: 124
<212> TYPE: PRT
<213> ORGANISM: Homo sapiens
<220> FEATURE:
<223> OTHER INFORMATION: anti-type III secretion system (TTSS) V antigen
      (anti-PcrV) antibody VH3 Vh region

<400> SEQUENCE: 29

Glu Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Pro Leu His Trp Val Arg Gln Ala Pro Gly Lys Gly Leu Glu Trp Val
        35                  40                  45

Ser Phe Ile Ser Tyr Asp Gly Ser Glu Lys Tyr Tyr Ala Ser Ser Val
    50                  55                  60

Lys Gly Arg Phe Thr Ile Ser Arg Asp Asn Ser Glu Asn Thr Leu Tyr
65                  70                  75                  80

Leu Gln Met Asn Ser Leu Arg Pro Glu Asp Thr Ala Val Tyr Tyr Cys
                85                  90                  95

Ala Arg Asn Arg Gly Asp Ile Tyr Tyr Asp Phe Thr Tyr Ala Met Asp
            100                 105                 110

Ile Trp Gly Gln Gly Thr Met Val Thr Val Ser Ser
        115                 120

<210> SEQ ID NO 30
<211> LENGTH: 106
<212> TYPE: PRT
<213> ORGANISM: Homo sapiens
<220> FEATURE:
<223> OTHER INFORMATION: anti-type III secretion system (TTSS) V antigen
      (anti-PcrV) antibody Vlambda subclass V-L region

<400> SEQUENCE: 30

Ser Ser Glu Leu Thr Gln Asp Pro Ala Val Ser Val Ala Leu Gly Gln
 1               5                  10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Gln His Phe Trp Ser Thr Pro Tyr Thr
                85                  90                  95

Phe Gly Gly Gly Thr Lys Leu Thr Val Leu
            100                 105

<210> SEQ ID NO 31
<211> LENGTH: 113
<212> TYPE: PRT
<213> ORGANISM: Homo sapiens
<220> FEATURE:
<223> OTHER INFORMATION: human germ-line VH1-18 antibody Vh region
```

-continued

```
<400> SEQUENCE: 31

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Thr Ala Val Tyr Tyr Cys
                85                  90                  95

Ala Arg Ala Phe Asp Ile Trp Gly Gln Gly Thr Met Val Thr Val Ser
            100                 105                 110

Ser

<210> SEQ ID NO 32
<211> LENGTH: 106
<212> TYPE: PRT
<213> ORGANISM: Homo sapiens
<220> FEATURE:
<223> OTHER INFORMATION: anti-type III secretion system (TTSS) V antigen
      (anti-PcrV) antibody Vlambda subclass V-L region

<400> SEQUENCE: 32

Ser Ser Glu Leu Thr Gln Asp Pro Ala Val Ser Val Ala Leu Gly Gln
1               5                   10                  15

Thr Val Thr Ile Thr Cys Gln Gly Asp Ser Leu Arg Ser Leu Tyr Ala
            20                  25                  30

Ser Trp Tyr Gln Gln Lys Pro Gly Gln Ala Pro Val Leu Val Leu Tyr
        35                  40                  45

Ser Lys Asn Ser Arg Pro Ser Gly Ile Pro Asp Arg Phe Ser Gly Ser
    50                  55                  60

Ser Ser Gly Asn Thr Ala Ser Leu Thr Ile Thr Gly Ala Arg Ala Glu
65                  70                  75                  80

Asp Glu Ala Asp Tyr Tyr Cys Gln His Phe Trp Ser Thr Pro Tyr Thr
                85                  90                  95

Phe Gly Gly Gly Thr Lys Leu Thr Val Leu
            100                 105

<210> SEQ ID NO 33
<211> LENGTH: 113
<212> TYPE: PRT
<213> ORGANISM: Homo sapiens
<220> FEATURE:
<223> OTHER INFORMATION: human germ-line VH3-30.3 antibody Vh region

<400> SEQUENCE: 33

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60
```

-continued

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ala Phe Asp Ile Trp Gly Gln Gly Thr Met Val Thr Val Ser
            100                 105                 110

Ser

<210> SEQ ID NO 34
<211> LENGTH: 109
<212> TYPE: PRT
<213> ORGANISM: Homo sapiens
<220> FEATURE:
<223> OTHER INFORMATION: anti-type III secretion system (TTSS) V antigen
      (anti-PcrV) antibody Vlambda subclass V-L region

<400> SEQUENCE: 34

Gln Ser Val Leu Thr Gln Pro Pro Ser Ala Ser Gly Ser Pro Gly Gln
 1               5                  10                  15

Ser Val Thr Ile Ser Cys Thr Gly Thr Ser Ser Asp Val Gly Ala Tyr
             20                  25                  30

Asn Tyr Val Ser Trp Tyr Gln Gln Tyr Pro Gly Lys Val Pro Lys Leu
         35                  40                  45

Ile Ile Tyr Glu Val Thr Lys Arg Pro Ser Gly Val Pro Asp Arg Phe
 50                  55                  60

Ser Gly Ser Lys Ser Gly Asn Thr Ala Ser Leu Thr Val Ser Gly Leu
 65                  70                  75                  80

Arg Ala Glu Asp Glu Ala Asp Tyr Tyr Cys Gln His Phe Trp Ser Thr
                 85                  90                  95

Pro Tyr Thr Phe Gly Gly Gly Thr Lys Leu Thr Val Leu
            100                 105

<210> SEQ ID NO 35
<211> LENGTH: 124
<212> TYPE: PRT
<213> ORGANISM: Homo sapiens
<220> FEATURE:
<223> OTHER INFORMATION: anti-type III secretion system (TTSS) V antigen
      (anti-PcrV) antibody VH3 Vh region

<400> SEQUENCE: 35

Glu Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Asn Tyr
             20                  25                  30

Pro Met His Trp Val Arg Gln Ala Pro Gly Lys Gly Leu Glu Trp Val
         35                  40                  45

Ala Val Ile Ser Tyr Asp Gly Ser Glu Lys Trp Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Glu Met Asn Ser Leu Arg Pro Glu Asp Thr Ala Val Tyr Tyr Cys
                 85                  90                  95

Ala Arg Asn Arg Gly Asp Ile Tyr Tyr Asp Phe Thr Tyr Ala Met Asp
            100                 105                 110

Tyr Trp Gly Gln Gly Thr Thr Val Thr Val Ser Ser
        115                 120
```

```
<210> SEQ ID NO 36
<211> LENGTH: 107
<212> TYPE: PRT
<213> ORGANISM: Homo sapiens
<220> FEATURE:
<223> OTHER INFORMATION: anti-type III secretion system (TTSS) V antigen
      (anti-PcrV) antibody VkappaI subclass V-L region

<400> SEQUENCE: 36

Asp Ile Gln Leu Thr Gln Ser Pro Ser Thr Leu Ser Ala Ser Val Gly
1               5                   10                  15

Asp Ser Val Thr Ile Thr Cys Arg Ala Ser Glu Gly Val Asp Arg Trp
            20                  25                  30

Leu Ala Trp Tyr Gln Gln Lys Pro Gly Arg Ala Pro Lys Leu Leu Ile
        35                  40                  45

Tyr Asp Ala Ser Thr Leu Gln Ser Gly Val Pro Ser Arg Phe Ser Gly
    50                  55                  60

Ser Gly Ser Gly Thr Glu Phe Ser Leu Thr Ile Ser Ser Leu Gln Pro
65                  70                  75                  80

Asp Asp Val Ala Thr Tyr Tyr Cys Gln His Phe Trp Ser Thr Pro Tyr
                85                  90                  95

Thr Phe Gly Gln Gly Thr Lys Leu Glu Ile Lys
            100                 105

<210> SEQ ID NO 37
<211> LENGTH: 107
<212> TYPE: PRT
<213> ORGANISM: Homo sapiens
<220> FEATURE:
<223> OTHER INFORMATION: anti-type III secretion system (TTSS) V antigen
      (anti-PcrV) antibody VkappaI subclass V-L region

<400> SEQUENCE: 37

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Arg Trp
            20                  25                  30

Val Ala Trp Tyr Gln Gln Arg Pro Gly Lys Ala Pro Asn Leu Leu Ile
        35                  40                  45

Tyr Asp Ala Ser Ser Leu Lys Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Ile Ala Thr Tyr Tyr Cys Gln Gln Phe Trp Gly Thr Pro Tyr
                85                  90                  95

Thr Phe Gly Gln Gly Thr Lys Leu Glu Ile Lys
            100                 105

<210> SEQ ID NO 38
<211> LENGTH: 15
<212> TYPE: PRT
<213> ORGANISM: Artificial Sequence
<220> FEATURE:
<223> OTHER INFORMATION: human germ-line JH6 antibody J-segment

<400> SEQUENCE: 38

Gly Met Asp Val Trp Gly Gln Gly Thr Thr Val Thr Val Ser Ser
1               5                   10                  15
```

```
<210> SEQ ID NO 39
<211> LENGTH: 107
<212> TYPE: PRT
<213> ORGANISM: Homo sapiens
<220> FEATURE:
<223> OTHER INFORMATION: human germ-line VkappaI L12 antibody V-L region

<400> SEQUENCE: 39

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
             20                  25                  30

Leu Ala Trp Tyr Gln Gln Lys Pro Gly Lys Ala Pro Lys Leu Leu Ile
         35                  40                  45

Tyr Asp Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Ser Tyr Ser Tyr
                 85                  90                  95

Thr Phe Gly Gln Gly Thr Lys Leu Glu Ile Lys
            100                 105

<210> SEQ ID NO 40
<211> LENGTH: 107
<212> TYPE: PRT
<213> ORGANISM: Homo sapiens
<220> FEATURE:
<223> OTHER INFORMATION: human germ-line VkappaIII antibody V-L region

<400> SEQUENCE: 40

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
             20                  25                  30

Leu Ala Trp Tyr Gln Gln Lys Pro Gly Gln Ala Pro Arg Leu Leu Ile
         35                  40                  45

Tyr Gly Ala Ser Thr Arg Ala Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Asn Asn Trp Pro Tyr
                 85                  90                  95

Thr Phe Gly Gln Gly Thr Lys Leu Glu Ile Lys
            100                 105

<210> SEQ ID NO 41
<211> LENGTH: 108
<212> TYPE: PRT
<213> ORGANISM: Homo sapiens
<220> FEATURE:
<223> OTHER INFORMATION: human germ-line Vlambda3 31 antibody V-L region

<400> SEQUENCE: 41

Ser Ser Glu Leu Thr Gln Asp Pro Ala Val Ser Val Ala Leu Gly Gln
 1               5                  10                  15

Thr Val Arg Ile Thr Cys Gln Gly Asp Ser Leu Arg Ser Tyr Tyr Ala
             20                  25                  30

Ser Trp Tyr Gln Gln Lys Pro Gly Gln Ala Pro Val Leu Val Ile Tyr
         35                  40                  45
```

```
Gly Lys Asn Asn Arg Pro Ser Gly Ile Pro Asp Arg Phe Ser Gly Ser
        50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Val Val Phe Gly Gly Gly Thr Lys Leu Thr Val Leu
                100                 105

<210> SEQ ID NO 42
<211> LENGTH: 111
<212> TYPE: PRT
<213> ORGANISM: Homo sapiens
<220> FEATURE:
<223> OTHER INFORMATION: human germ-line Vlambda2 2c antibody V-L region

<400> SEQUENCE: 42

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Glu Val Ser Lys Arg Pro Ser Gly Val Pro Asp Arg Phe
        50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Ser
                85                  90                  95

Asn Asn Phe Val Val Phe Gly Gly Gly Thr Lys Leu Thr Val Leu
                100                 105                 110

<210> SEQ ID NO 43
<211> LENGTH: 108
<212> TYPE: PRT
<213> ORGANISM: Homo sapiens
<220> FEATURE:
<223> OTHER INFORMATION: anti-type III secretion system (TTSS) V antigen
      (anti-PcrV) antibody VkappaIII subclass V-L region

<400> SEQUENCE: 43

Glu Ile Val Leu Thr Gln Phe Pro Gly Thr Leu Ser Leu Ser Pro Gly
1               5                   10                  15

Glu Arg Ala Thr Leu Ser Cys Arg Ala Ser Asn Ser Val Gly Ala Tyr
                20                  25                  30

Asn Leu Ala Trp Tyr Gln Gln Lys Pro Gly Gln Ala Pro Arg Leu Leu
            35                  40                  45

Ile Tyr Gly Ala Ser Arg Arg Ala Pro Gly Ile Pro Asp Arg Phe Ser
        50                  55                  60

Gly Ser Gly Ser Gly Thr Asp Phe Thr Leu Thr Ile Asn Arg Leu Glu
65                  70                  75                  80

Pro Glu Asp Phe Ala Val Tyr Tyr Cys Gln Gln Phe Trp Ser Thr Pro
                85                  90                  95

Tyr Thr Phe Gly Gln Gly Thr Lys Leu Glu Ile Lys
                100                 105

<210> SEQ ID NO 44
<211> LENGTH: 109
<212> TYPE: PRT
<213> ORGANISM: Homo sapiens
```

<220> FEATURE:
<223> OTHER INFORMATION: anti-type III secretion system (TTSS) V antigen
      (anti-PcrV) antibody Vlambda2 subclass V-L region

<400> SEQUENCE: 44

Gln Ser Val Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Ala Tyr
            20                  25                  30

Asn Tyr Val Ser Trp Tyr Gln Gln Tyr Pro Gly Lys Val Pro Lys Leu
        35                  40                  45

Ile Ile Tyr Glu Val Thr Lys Arg Pro Ser Gly Val Pro Asp Arg Phe
    50                  55                  60

Ser Gly Ser Lys Ser Gly Asn Thr Ala Ser Leu Thr Val Ser Gly Arg
65                  70                  75                  80

Gln Ala Glu Asp Glu Ala Asp Tyr Tyr Cys Gln His Phe Trp Ser Thr
                85                  90                  95

Pro Tyr Thr Phe Gly Gly Gly Thr Lys Leu Thr Val Leu
            100                 105

<210> SEQ ID NO 45
<211> LENGTH: 15
<212> TYPE: PRT
<213> ORGANISM: Artificial Sequence
<220> FEATURE:
<223> OTHER INFORMATION: synthetic anti-type III secretion system (TTSS)
      V antigen (anti-PcrV) antibody V-H
      complementarity-determining region 3 (CDR3)
<220> FEATURE:
<221> NAME/KEY: VARIANT
<222> LOCATION: (15)...(15)
<223> OTHER INFORMATION: Xaa = Ile, Gln, Tyr or Ser

<400> SEQUENCE: 45

Asn Arg Gly Asp Ile Tyr Tyr Asp Phe Thr Tyr Ala Met Asp Xaa
1               5                   10                  15

<210> SEQ ID NO 46
<211> LENGTH: 5
<212> TYPE: PRT
<213> ORGANISM: Artificial Sequence
<220> FEATURE:
<223> OTHER INFORMATION: synthetic anti-type III secretion system (TTSS)
      V antigen (anti-PcrV) antibody V-L
      complementarity-determining region 3 (CDR3)
<220> FEATURE:
<221> NAME/KEY: VARIANT
<222> LOCATION: (3)...(3)
<223> OTHER INFORMATION: Xaa = Ser or Gly

<400> SEQUENCE: 46

Phe Trp Xaa Thr Pro
1               5

<210> SEQ ID NO 47
<211> LENGTH: 9
<212> TYPE: PRT
<213> ORGANISM: Artificial Sequence
<220> FEATURE:
<223> OTHER INFORMATION: synthetic anti-type III secretion system (TTSS)
      V antigen (anti-PcrV) antibody V-L
      complementarity-determining region 3 (CDR3)

<400> SEQUENCE: 47

Gln Gln Phe Trp Ser Thr Pro Tyr Thr
1               5

```
<210> SEQ ID NO 48
<211> LENGTH: 9
<212> TYPE: PRT
<213> ORGANISM: Artificial Sequence
<220> FEATURE:
<223> OTHER INFORMATION: synthetic anti-type III secretion system (TTSS)
      V antigen (anti-PcrV) antibody V-L
      complementarity-determining region 3 (CDR3)

<400> SEQUENCE: 48

Gln His Phe Trp Gly Thr Pro Tyr Thr
1               5

<210> SEQ ID NO 49
<211> LENGTH: 9
<212> TYPE: PRT
<213> ORGANISM: Artificial Sequence
<220> FEATURE:
<223> OTHER INFORMATION: synthetic anti-type III secretion system (TTSS)
      V antigen (anti-PcrV) antibody V-L
      complementarity-determining region 3 (CDR3)

<400> SEQUENCE: 49

Gln His Phe Trp Ser Thr Pro Tyr Thr
1               5

<210> SEQ ID NO 50
<211> LENGTH: 15
<212> TYPE: PRT
<213> ORGANISM: Artificial Sequence
<220> FEATURE:
<223> OTHER INFORMATION: synthetic anti-type III secretion system (TTSS)
      V antigen (anti-PcrV) antibody V-H
      complementarity-determining region 3 (CDR3)

<400> SEQUENCE: 50

Asn Arg Gly Asp Ile Tyr Tyr Asp Phe Thr Tyr Ala Met Asp Ile
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: synthetic anti-type III secretion system (TTSS)
      V antigen (anti-PcrV) antibody V-H
      complementarity-determining region 3 (CDR3)

<400> SEQUENCE: 51

Asn Arg Gly Asp Ile Tyr Tyr Asp Phe Thr Tyr Ala Met Asp Gln
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: synthetic anti-type III secretion system (TTSS)
      V antigen (anti-PcrV) antibody V-H
      complementarity-determining region 3 (CDR3)

<400> SEQUENCE: 52

Asn Arg Gly Asp Ile Tyr Tyr Asp Phe Thr Tyr Ala Met Asp Tyr
1               5                   10                  15

<210> SEQ ID NO 53
<211> LENGTH: 15
<212> TYPE: PRT
<213> ORGANISM: Artificial Sequence
```

```
<220> FEATURE:
<223> OTHER INFORMATION: synthetic anti-type III secretion system (TTSS)
      V antigen (anti-PcrV) antibody V-H
      complementarity-determining region 3 (CDR3)

<400> SEQUENCE: 53

Asn Arg Gly Asp Ile Tyr Tyr Asp Phe Thr Tyr Ala Met Asp Ser
1               5                   10                  15

<210> SEQ ID NO 54
<211> LENGTH: 11
<212> TYPE: PRT
<213> ORGANISM: Artificial Sequence
<220> FEATURE:
<223> OTHER INFORMATION: synthetic anti-type III secretion system (TTSS)
      V antigen (anti-PcrV) antibody V-H
      complementarity-determining region 3 (CDR3)
      minimal essential binding specificity determinamt (BSD)

<400> SEQUENCE: 54

Asn Arg Gly Asp Ile Tyr Tyr Asp Phe Thr Tyr
1               5                   10

<210> SEQ ID NO 55
<211> LENGTH: 15
<212> TYPE: PRT
<213> ORGANISM: Artificial Sequence
<220> FEATURE:
<223> OTHER INFORMATION: synthetic anti-type III secretion system (TTSS)
      V antigen (anti-PcrV) antibody V-H
      complementarity-determining region 3 (CDR3)
<220> FEATURE:
<221> NAME/KEY: VARIANT
<222> LOCATION: (13)...(13)
<223> OTHER INFORMATION: Xaa = Met or Phe
<220> FEATURE:
<221> NAME/KEY: VARIANT
<222> LOCATION: (15)...(15)
<223> OTHER INFORMATION: Xaa = Ile, Ser or Gln

<400> SEQUENCE: 55

Asn Arg Gly Asp Ile Tyr Tyr Asp Phe Thr Tyr Ala Xaa Asp Xaa
1               5                   10                  15

<210> SEQ ID NO 56
<211> LENGTH: 5
<212> TYPE: PRT
<213> ORGANISM: Artificial Sequence
<220> FEATURE:
<223> OTHER INFORMATION: synthetic anti-type III secretion system (TTSS)
      V antigen (anti-PcrV) antibody V-H
      complementarity-determining region 1 (CDR1)

<400> SEQUENCE: 56

Asn Tyr Pro Met His
1               5

<210> SEQ ID NO 57
<211> LENGTH: 17
<212> TYPE: PRT
<213> ORGANISM: Artificial Sequence
<220> FEATURE:
<223> OTHER INFORMATION: synthetic anti-type III secretion system (TTSS)
      V antigen (anti-PcrV) antibody V-H
      complementarity-determining region 2 (CDR2)

<400> SEQUENCE: 57

Val Ile Ser Tyr Asp Gly Ser Glu Lys Trp Tyr Ala Asp Ser Val Lys
1               5                   10                  15

Gly
```

-continued

```
<210> SEQ ID NO 58
<211> LENGTH: 11
<212> TYPE: PRT
<213> ORGANISM: Artificial Sequence
<220> FEATURE:
<223> OTHER INFORMATION: synthetic anti-type III secretion system (TTSS)
      V antigen (anti-PcrV) antibody V-L
      complementarity-determining region 1 (CDR1)

<400> SEQUENCE: 58

Arg Ala Ser Glu Gly Val Asp Arg Trp Leu Ala
 1               5                  10

<210> SEQ ID NO 59
<211> LENGTH: 7
<212> TYPE: PRT
<213> ORGANISM: Artificial Sequence
<220> FEATURE:
<223> OTHER INFORMATION: synthetic anti-type III secretion system (TTSS)
      V antigen (anti-PcrV) antibody V-L
      complementarity-determining region 2 (CDR2)

<400> SEQUENCE: 59

Asp Ala Ser Thr Leu Gln Ser
 1               5
```